US012796911B2

(12) United States Patent
Drozdov et al.

(10) Patent No.: US 12,796,911 B2
(45) Date of Patent: Nov. 17, 2026

(54) MYOPIA PROTOCOLS USING A DIGITAL DISPLAY

(71) Applicant: Blink O.G. Ltd., Haifa (IL)

(72) Inventors: Gilad Drozdov, Haifa (IL); Oren Haimovitch-Yogev, Haifa (IL)

(73) Assignee: BLINK TECHNOLOGIES INC., Palo Alto, CA (US)

( * ) Notice: Subject to any disclaimer, the term of this patent is extended or adjusted under 35 U.S.C. 154(b) by 229 days.

(21) Appl. No.: 18/774,974

(22) Filed: Jul. 17, 2024

(65) Prior Publication Data

US 2025/0040801 A1 Feb. 6, 2025

Related U.S. Application Data

(60) Provisional application No. 63/527,625, filed on Jul. 19, 2023.

(51) Int. Cl.
*A61B 3/028* (2006.01)
*G06T 7/00* (2017.01)
*G16H 20/00* (2018.01)

(52) U.S. Cl.
CPC ............ *A61B 3/028* (2013.01); *G06T 7/0012* (2013.01); *G16H 20/00* (2018.01); *G06T 2207/10016* (2013.01); *G06T 2207/30041* (2013.01)

(58) Field of Classification Search
CPC .................. A61B 3/028; G06T 7/0012; G06T 2207/10016; G06T 2207/30041; G06T 2207/30201; G16H 20/00
USPC .......................................................... 351/222
See application file for complete search history.

(56) References Cited

U.S. PATENT DOCUMENTS

| | | | | |
|---|---|---|---|---|
| 12,298,600 B2 * | 5/2025 | Zheleznyak | G02C 7/027 | |
| 2007/0159601 A1 * | 7/2007 | Ho | G02C 7/02 | 351/221 |
| 2013/0265541 A1 * | 10/2013 | Zhou | A61B 3/0041 | 351/205 |
| 2017/0055825 A1 * | 3/2017 | Tumlinson | A61B 3/0025 | |
| 2022/0007929 A1 * | 1/2022 | Padula | A61B 3/0008 | |
| 2022/0351638 A1 * | 11/2022 | Wu | A61B 3/028 | |
| 2023/0218163 A1 * | 7/2023 | Hunter | A61B 3/032 | 351/213 |

* cited by examiner

*Primary Examiner* — William R Alexander
(74) *Attorney, Agent, or Firm* — AlphaPatent Associates Ltd.; Daniel J. Swirsky

(57) ABSTRACT

A digital display system to administer a myopia protocol, the system utilizing a forward-looking camera, a digital display, and processor to process digital media, face and eye landmark images, and determine the viewer-to-display distance, where the data is used to calculate a cone of vision, infer a fixation region, and receive a visual blurring function, where the system determines an area of interest in each image based on eye-tracking data and applies the visual blurring function to the area of interest using the visual blurring function, thereby providing a personalized, interactive experience complimenting traditional myopia protocols.

47 Claims, 33 Drawing Sheets

MYOPIA PROTOCOLS USING A DIGITAL DISPLAY

CROSS REFERENCE TO RELATED APPLICATIONS

The present application claims priority to U.S. Provisional Patent Application No. 63/527,625 filed on Jul. 19, 2023, the disclosure of which is incorporated herein by reference in its entirety.

FIELD

The present disclosure relates to a system for administering a myopia protocol and methods thereof. The system is designed to monitor the quality of the administration of the myopia protocol session(s), wherein the quality is a function of a person's position relative to a digital display, a duration of the interaction of the viewer with the modified displayed media, and the user compliance with the myopia protocol. The system provides a consistent blurring function in the region of fixation on the digital display, tailored to coincide with the viewer's position.

The present disclosure includes provisions to develop a personalized treatment protocol. This personalized treatment protocol includes a unique blurring function that is influenced by the severity of the myopia, the viewer's distance from the display, and the viewer's response to the administration of treatment. The personalized treatment protocol allows for, or may support, conventional myopia treatment protocols.

BACKGROUND

Treating myopia presents several challenges, primarily due to its complex nature and the varying degree of severity among patients. The common approach has been using corrective lenses such as glasses or contact lenses. While previously these methods were seen as addressing symptoms without halting the progression of the condition, breakthroughs in lens technology have begun to challenge this perspective. A significant example is the Essilor® Stellest™ lens by EssilorLuxottica, which has shown strong efficacy in slowing myopia progression and axial elongation, according to three-year clinical trial results. Conducted at the Eye Hospital of Wenzhou Medical University in Wenzhou, China, the trial found that children using these highly aspherical lenslet (HAL) spectacles saved more than one diopter of myopia on average over three years, even proving effective in older children. Furthermore, full-time wear of Essilor® Stellest™ lenses resulted in a marked increase in myopia control efficacy.

Managing myopia, particularly in children, poses distinct challenges due to the practical difficulties of consistent eyewear use and the gaps in monitoring between office visits. Children often find it challenging to regularly wear glasses, whether due to discomfort, self-consciousness, or the physical hindrance during active play. The application and removal of contact lenses can also be daunting for young individuals, making consistent usage more difficult to achieve. These factors can lead to inadequate corrective lens wear, compromising the effectiveness of the myopia treatment protocol.

Furthermore, the periodic nature of office visits poses a challenge in the continuous monitoring of myopia progression. While an eye care professional can prescribe a treatment based on a diagnosed condition at the time of the visit, they lack real-time information on adherence to the treatment protocol, and any changes in vision or eye health that may occur between visits. This intermittent visibility can make it challenging to identify and address issues promptly, such as non-compliance with eyewear use or the unsuitability of a given treatment, potentially leading to less effective management of the child's myopia. It can also be challenging to gather data between visits that would be useful in making breakthroughs in treatment protocols for patients with myopia. Therefore, achieving consistent usage of corrective eyewear and improving the continuity of monitoring are vital in enhancing myopia management, especially in the pediatric population.

As we advance further into the digital age, computer displays have become ubiquitous in our daily lives. From education to entertainment, work to social interaction, these digital platforms play a central role, shaping the way we learn, communicate, and engage with the world. This trend is particularly evident among children, who are now growing up in an era where screens are often their primary means of accessing information and interacting with their peers.

Yet, this widespread use of digital displays also presents unique opportunities in healthcare, specifically in the treatment and monitoring of conditions such as myopia. Given the significant time children spend in front of screens, adapting these digital displays with myopia treatment protocols could potentially revolutionize the approach to managing this common vision disorder.

For instance, incorporating an individualized myopia treatment protocol into a digital display system could allow for real-time monitoring of the progression of myopia and provide immediate treatment adaptations based on the user's visual needs. This could include adjusting the visual content, applying spatial blurring attributes, or providing prompts to encourage breaks or changes in viewing distance, all personalized to the viewer's specific condition.

Furthermore, the use of digital displays for myopia treatment could also enhance patient compliance, as the treatment becomes integrated into their everyday activities, rather than being seen as an additional task or responsibility. By leveraging the widespread use of digital displays, especially among children, the present disclosure includes systems and methods for monitoring compliance, determining the effectiveness of a myopia treatment protocol, and opportunities to modify a myopia protocol to deliver positive outcomes more reliably in myopia patients. The present disclosure further provides opportunities to incorporate glasses and other eye wear, e.g., contact lenses, as well as prescription pharmaceuticals for more effective myopia management and prevention. Accordingly, the present application provides improved face landmark detection, eye tracking, and camera image evaluation for more accurate and efficient processing and rendering of 3D projections from 3D displays allowing for the diagnosis and treatment of myopia.

SUMMARY

Embodiments of the present disclosure may include a method for modifying digital media to be displayed on a digital display as part of a myopia protocol, the method including receiving digital media. Embodiments may also include receiving face image data, eye landmark image data for a viewer within a field of view of at least one camera in proximity to a viewer, and a distance between the digital display and the viewer.

Embodiments may also include determining a cone of vision. In some embodiments, the gaze direction, the cone of vision, and distance between the digital display and the viewer may be used to infer a region of fixation. Embodiments may also include receiving a visual blurring function for each eye of the viewer. Embodiments may also include determining a count of images and an area of interest within the boundaries of a frame of each image, the area of interest based at least in part on the eye tracking information. Embodiments may also include applying a spatial blurring attribute for the count of images for each eye of the viewer based at least in part on the received visual blurring function of the viewer, the determined area of interest, and the myopia protocol.

In some embodiments, the myopia protocol may be at least one of a myopia diagnosis protocol, a myopia treatment protocol, and a quality of treatment protocol. In some embodiments, the myopia diagnosis protocol may be based at least in part on a visual acuity test, a refraction test, a retinoscopy, an autorefractor, and a dilated eye exam. In some embodiments, the myopia treatment protocol may include use of prescription eyeglasses, prescription contact lenses, and an orthokeratology.

In some embodiments, the myopia treatment protocol may include use of prescription eyeglasses, prescription contact lenses, and an orthokeratology outside of a viewing session. In some embodiments, the modified digital media may be displayed on the digital display. In some embodiments, the quality of treatment protocol may include receiving a viewer performance benchmark. Embodiments may also include displaying the spatial blurring attribute for the count of images for each eye of the viewer based at least in part on the received visual blurring function of the viewer and the myopia protocol. Embodiments may also include determining a session performance of the viewer based at least in part on the displayed spatial blurring attribute for the count of images for each eye of the viewer. Embodiments may also include comparing the viewer performance benchmark with the session performance.

In some embodiments, the method, may include determining a viewing duration threshold. In some embodiments, the determining may be based at least in part on the duration. In some embodiments, the inferred region of fixation matches the two-dimensional distribution of the projections for each eye of the viewer. Embodiments may also include comparing the viewing duration threshold with the viewer performance benchmark. Embodiments may also include assigning a session performance value based on the comparison. Embodiments may also include storing the session performance of the viewer in memory.

Embodiments may also include receiving a viewer performance benchmark may include a minimum viewing duration threshold. Embodiments may also include determining a session performance of the viewer based at least in part on the displayed spatial blurring attribute for the count of images for each eye of the viewer may include determining a viewing duration threshold. In some embodiments, the determining may be based at least in part on the duration.

In some embodiments, the inferred region of fixation matches the two-dimensional distribution of the projections for each eye of the viewer. Embodiments may also include comparing the viewing duration threshold with the minimum viewing duration threshold. Embodiments may also include assigning a session performance value based on the comparison.

In some embodiments, the quality of treatment protocol may include associating at least one parameter of the quality of treatment protocol with a viewer profile. In some embodiments, the at least one parameter of the quality of treatment protocol may include a current visual acuity measurement. Embodiments may also include an indication of a progression status of a myopia condition. Embodiments may also include an eye health examination. Embodiments may also include a compliance parameter. Embodiments may also include a myopia treatment prescription. Embodiments may also include a session performance value.

Embodiments may also include receiving digital media may include opening a media viewing application. Embodiments may also include receiving user credentials associated with a viewer profile. Embodiments may also include loading the digital media in the media viewing application. Embodiments may also include a media viewing application may be a myopia treatment application.

Embodiments may also include receiving digital media may include receiving at a processor digital media from at least one of a streaming service, a dedicated media device, a video gaming console, an online gaming service, a social media site, and a live streaming service. In some embodiments, the digital media may be at least one of a podcast, a social media post, a live streaming event, a video game, a webpage, an e-book, a video call, augmented reality information, and a virtual reality environment.

In some embodiments, the digital media may be at least one of a still image, a video, a movie, a television program, a social media content, and specialized content for the treatment of myopia. Embodiments may also include receiving digital media may include receiving the digital media at a processor via one or more of a wireless streaming service, a connected media player, a connected laptop, a connected remote server, and a local server.

Embodiments may also include receiving a visual blurring function of the viewer may include receiving a contrast sensitivity function (CSF) indicative of a visual acuity field of the viewer. Embodiments may also include a contrast sensitivity function (CSF) indicative of a visual acuity of the viewer may include data indicative of a performance of a contrast function sensitivity performance.

Embodiments may also include a contrast sensitivity function (CSF) indicative of a visual acuity of the viewer may include a mathematical function for a Visual Blurring Function (VBF) as a function of time. In some embodiments, the mathematical function may include at least one variable for each of a treatment function for each eye of the viewer.

Embodiments may also include a two-dimensional boundary of a Point of Regard for each eye of the viewer. Embodiments may also include a distance between at least one eye of the viewer and the two-dimensional boundary of the area of focus for at least one eye of the viewer. Embodiments may also include at least one projection.

In some embodiments, the method, may include rendering a first two-dimensional treatment area for each eye of the viewer based at least in part on the mathematical function at time $t_0$. Embodiments may also include displaying the rendering of the first two-dimensional treatment area for each eye of the viewer. Embodiments may also include determining a visual acuity field for each eye of the viewer in response to the displayed rendering of the first treatment area for each eye of the viewer at time $t_0$.

In some embodiments, the method may include comparing the visual acuity performance for each eye of the viewer at time t0 with a historical visual acuity performance for each eye of the viewer. Embodiments may also include updating the visual blurring function for at least one eye of the viewer if the comparison indicates a change in the visual acuity performance the viewer's eye(s).

In some embodiments, the updating the visual blurring function for at least one eye of the viewer if the comparison indicates a change in the visual acuity performance for the at least one eye, the change in visual acuity may include at least one of an indication of an improvement in visual acuity and a deterioration in visual acuity. Embodiments may also include a contrast sensitivity function (CSF) indicative of a visual acuity of the viewer may include data indicative of a performance of a spatial frequency sensitivity performance.

Embodiments may also include a contrast sensitivity function (CSF) indicative of a visual acuity of the viewer may include a function indicative of a visual acuity performance of the user at a distance from the digital display and its minimal Spatial Frequency Threshold for a trackable object on the digital display. Embodiments may also include receiving a visual blurring function of the viewer may include receiving viewer digital identification data indicative of the viewer. Embodiments may also include transmitting a request for a visual acuity profile of the viewer. Embodiments may also include receiving the visual acuity profile. In some embodiments, the visual acuity profile includes at least the visual blurring function of the viewer and a myopia treatment protocol.

Embodiments may also include receiving the visual acuity profile may include a myopia assessment for each eye of the viewer. Embodiments may also include receiving a visual blurring function of the viewer may include receiving a contrast sensitivity function (CSF). In some embodiments, the contrast sensitivity function (CSF) may include at least one instruction for applying the spatial blurring attribute based at least in part on the received visual blurring function of the viewer and the myopia protocol.

Embodiments may also include applying a spatial blurring attribute for the count of images for each eye of the viewer based at least in part on the received visual blurring function of the viewer and the myopia protocol may include at least one instruction for determining the spatial blurring attribute for the count of images for each eye of the viewer based at least in part on one or more visual acuity fields of the viewer, the one or more visual acuity field. In some embodiments, the visual acuity field may include at least one of a foveal visual acuity field. Embodiments may also include a parafoveal visual acuity field. Embodiments may also include a peripheral visual acuity field.

In some embodiments, the method may include displaying the count of images for each eye of the viewer based on the received visual blurring function of the viewer. Embodiments may also include displaying the count of images for each eye of the viewer based on the received visual blurring function of the viewer may include dynamically altering the spatial blurring attribute for the count of images for each eye of the viewer as a function of time.

Embodiments may also include dynamically altering the spatial blurring attribute for the count of images for each eye of the viewer as a function of time may include altering the dimensions of the area of the spatial blurring attribute within the foveal visual acuity field of an eye of the viewer as a function of time. Embodiments may also include altering the dimensions of the area of the spatial blurring attribute to maintain a cognitive load may include inferring the cognitive load from the eye tracking information.

Embodiments may also include dynamically altering the spatial blurring attribute for the count of images for each eye of the viewer as a function of time may include altering the dimensions of the area of the spatial blurring attribute within the foveal visual acuity field of an eye of the viewer as a sinusoidal function of time. Embodiments may also include dynamically altering the spatial blurring attribute for the count of images for each eye of the viewer as a function of time may include altering the dimensions of the area of the spatial blurring attribute within the foveal visual acuity field of an eye of the viewer. In some embodiments, altering the dimensions of the area of the spatial blurring attribute to maintain a cognitive load.

Embodiments may also include applying a spatial blurring attribute for the count of images for each eye of the viewer based at least in part on the received visual blurring function of the viewer and the myopia protocol may include determining the count of images based at least in part on one or more of a refresh rate of the digital display, a defined segment of video, a sampling rate of at least one camera of the digital display, and the visual blurring function for each eye of the viewer.

Embodiments may also include applying a spatial blurring attribute for the count of images for each eye of the viewer based at least in part on the received visual blurring function of the viewer and the myopia protocol may include using the eye tracking information to determine an area of interest of the digital display. Embodiments may also include correlating the area of interest of the digital display to the count of images for each eye of the viewer. Embodiments may also include applying the visual blurring function of the viewer to an area of interest of a projected image for at least one eye of the viewer.

Embodiments may also include applying the visual blurring function of the viewer to an area of interest of a projected image for the at least one eye of the viewer may include spatially-adjusting the area of interest of the projected image for the at least one eye based at least in part on the myopia treatment protocol. In some embodiments, the method may include using the eye tracking information to determine an area of interest via the point-of-regard of the digital display. Embodiments may also include correlating the area of interest of the digital display to the count of images and the distribution of projections for each eye of the viewer.

Embodiments may also include applying the visual blurring function of the viewer to an area of interest of a projected image for at least one eye of the viewer. Embodiments may also include spatially-adjusting the area of interest of the projected image for the at least one eye. Embodiments may also include displaying the count of images for each eye of the viewer based on the received visual blurring function of the viewer.

Embodiments may also include spatially-adjusting the area of interest of the projected image for the at least one eye may include temporally-adjusting the application of the visual blurring function of the viewer to the area of interest of the projected image for at least one eye of the viewer. Embodiments may also include monitoring the accumulated period. In some embodiments, the visual blurring function of the viewer may be applied to the area of interest of the projected image for at least one eye of the viewer.

In some embodiments, the method may include using the eye tracking information to determine an area of interest via the point-of-regard of the digital display. Embodiments may also include correlating the area of interest of the digital display to the count of images and the distribution of projections for each eye of the viewer.

Embodiments may also include applying the visual blurring function of the viewer to an area of interest of a projected image for at least one eye of the viewer. Embodiments may also include temporally-adjusting the area of interest of the projected image for the at least one eye. Embodiments may also include displaying the count of images for each eye of the viewer based on the received visual blurring function of the viewer.

In some embodiments, the method may include monitoring the accumulated period. In some embodiments, the visual blurring function of the viewer may be applied to the area of interest of the projected image for at least one eye of the viewer. In some embodiments, the method may include assessing a quality of treatment protocol.

Embodiments may also include a quality of treatment protocol may include receiving a viewer performance benchmark. Embodiments may also include displaying temporally-adjusting the area of interest of the projected image for the at least one eye based at least in part on the received visual blurring function of the viewer and the myopia protocol. Embodiments may also include determining a session performance of the viewer based at least in part on the displayed spatial blurring attribute for the count of images for each eye of the viewer. Embodiments may also include comparing the viewer performance benchmark with the session performance.

In some embodiments, the method, may include determining a viewing duration threshold. In some embodiments, the determining may be based at least in part on the duration. In some embodiments, the inferred region of fixation matches the two-dimensional distribution of the projections for each eye of the viewer. Embodiments may also include comparing the viewing duration threshold with the viewer performance benchmark. Embodiments may also include assigning a session performance value based on the comparison. Embodiments may also include storing the session performance of the viewer in memory.

Embodiments may also include receiving a viewer performance benchmark may include a minimum viewing duration threshold. Embodiments may also include determining a session performance of the viewer based at least in part on the displayed spatial blurring attribute for the count of images for each eye of the viewer may include determining a viewing duration threshold. In some embodiments, the determining may be based at least in part on the duration.

In some embodiments, the inferred region of fixation matches the two-dimensional distribution of the projections for each eye of the viewer. Embodiments may also include comparing the viewing duration threshold with the minimum viewing duration threshold. Embodiments may also include assigning a session performance value based on the comparison.

Embodiments of the present disclosure may include a method for assessing a visual acuity of a viewer of a digital display as part of a myopia protocol, the method including projecting a first sequence of images containing at least one object of intertest. In some embodiments, the viewer may be a known first distance from the digital display. Embodiments may also include determining a first area of interest of each eye of the viewer via a point of regard.

Embodiments may also include determining a first level of fixation of each eye of the viewer. Embodiments may also include correlating the determined area of interest of each eye of the viewer with the determined fixation of each eye of the viewer. Embodiments may also include using the digital display to project a second sequence of image containing at least one object of intertest in a second location.

In some embodiments, the viewer may be a known second distance from the digital display. Embodiments may also include determining a second area of interest of each eye of the viewer. Embodiments may also include determining a second level of fixation of each eye of the viewer. Embodiments may also include correlating the determined area of interest of each eye of the viewer with the determined second area of fixation of each eye of the viewer. Embodiments may also include assessing an ability of the viewer to follow a movement of the at least one object of interest towards the second location and an ability of the viewer to fixate on the at least one object.

In some embodiments, the method for assessing the visual acuity of a viewer of a digital display may include rendering a diagnosis of myopia based at least in part on the assessment of the ability of the viewer to follow a movement of the at least one object of interest towards the second location and an ability of the viewer to fixate on the at least one object.

In some embodiments, the method may include prescribing a prescription for a treatment of myopia using a digital display. In some embodiments, the prescription may include a visual blurring function for each of the eyes of the viewer. Embodiments may also include a myopia treatment protocol.

In some embodiments, the visual blurring function for each of the eyes of the viewer may be associated with the viewer in a digital record, the digital record including at least one of a viewer identification, an age-appropriate content for 3D display, an interest appropriate content for 3D display, insurance carrier information, a prescribing medical professional, and an access frequency for administering treatment.

In some embodiments, the myopia protocol may include use of prescription eyeglasses, prescription contact lenses, or an orthokeratology in addition to a myopia treatment protocol using a digital display. In some embodiments, the method may include assessing a quality of treatment protocol. Embodiments may also include a quality of treatment protocol may include receiving a viewer performance benchmark. Embodiments may also include displaying a temporally-adjusted area of interest of the projected image for the at least one eye based at least in part on the received visual blurring function of the viewer and the myopia protocol. Embodiments may also include determining a session performance of the viewer based at least in part on the displayed spatial blurring attribute for the count of images for each eye of the viewer. Embodiments may also include comparing the viewer performance benchmark with the session performance.

In some embodiments, the method may include storing the session performance of the viewer and the comparison of the viewer performance benchmark with the session performance to a digital viewer profile record. In some embodiments, the method, may include determining a viewing duration threshold. In some embodiments, the determining may be based at least in part on the duration. In some embodiments, the inferred region of fixation matches the two-dimensional distribution of the projections for each eye of the viewer. Embodiments may also include comparing the viewing duration threshold with the viewer performance benchmark. Embodiments may also include assigning a session performance value based on the comparison. Embodiments may also include storing the session performance of the viewer in memory.

Embodiments may also include receiving a viewer performance benchmark may include a viewer performance of the viewer at a first distance and at least one second distance. Embodiments may also include receiving a viewer performance benchmark may include a minimum viewing duration threshold. Embodiments may also include determining a session performance of the viewer based at least in part on the displayed spatial blurring attribute for the count of images for each eye of the viewer may include determining a viewing duration threshold. In some embodiments, the determining may be based at least in part on the duration.

In some embodiments, the inferred region of fixation matches the two-dimensional distribution of the projections for each eye of the viewer. Embodiments may also include comparing the viewing duration threshold with the minimum viewing duration threshold. Embodiments may also include assigning a session performance value based on the comparison.

Embodiments of the present disclosure may include a method for treating myopia using a digital display, the method including receiving a visual blurring function for a first eye of the viewer. Embodiments may also include determining a gaze direction, a distance between the viewer and the digital display, and the point of regard of the first eye of the viewer with regard to the digital display.

Embodiments may also include rendering a dynamic viewing session containing at least one area of interest. In some embodiments, the dynamic viewing session may include a plurality of images for display by the digital display for the first eye, the rendering based at least in part on the visual blurring function for the first eye, the determined gaze direction, the distance between the viewer and the digital display, and the point of regard of the first eye of the viewer, and the at least one area of interest.

Embodiments may also include performing an assessment of an ability of the first eye to follow a movement of the at least one area of interest and an ability of the first eye of the viewer to fixate on the at least one object. Embodiments may also include adjusting spatially and temporally the at least one area of interest in the rendered dynamic viewing session based at least in part on the assessment.

In some embodiments, the method, the method further including determining a distance between the viewer and the digital display. Embodiments may also include receiving a visual blurring function for a second eye of the viewer. Embodiments may also include determining a gaze direction and the point of regard of the second eye of the viewer with regard to the digital display.

Embodiments may also include rendering a dynamic viewing session containing at least one area of interest. In some embodiments, the dynamic viewing session may include a plurality of images for display by the digital display for the second eye, the rendering based at least in part on the visual blurring function for the second eye, the determined gaze direction and the point of regard of the second eye of the viewer, the distance between the viewer and the digital display, and the at least one area of interest.

Embodiments may also include performing an assessment of an ability of the second eye to follow a movement of the at least one area of interest and an ability of the second eye of the viewer to fixate on the at least one area of interest at the distance. Embodiments may also include adjusting spatially and temporally the at least one area of interest in the rendered dynamic viewing session based at least in part on the assessment.

In some embodiments, the method, the method further including conducting a calibration of digital display. Embodiments may also include conducting a calibration of digital display may include obtaining face image data and eye landmark image data for a viewer within a field of view of at least one camera in proximity to a digital display. Embodiments may also include detecting face and eye landmarks for the viewer in one or more image frames based on the face image data.

Embodiments may also include determining head pose information based on the face image data and eye landmark image data. Embodiments may also include determining eye tracking information for the viewer based on the face image data, eye landmark image data, and head pose information, the eye tracking information including a point of regard (PoR) of each eye of the viewer.

Embodiments may also include eye state of each eye of the viewer. Embodiments may also include gaze direction of each eye of the viewer. Embodiments may also include eye landmark illumination information for each eye of the viewer. Embodiments may also include a position of each eye of the viewer relative to the digital display.

Embodiments of the present disclosure may also include a computer program product including instructions which, when executed by a computer, cause the computer to carry out the following steps obtaining face image data and eye landmark image data for a viewer within a field of view of at least one camera in proximity to a digital display. Embodiments may also include obtaining a distance between the viewer and the digital display.

Embodiments may also include determining a point of regard of the viewer of the digital display. Embodiments may also include associating the point of regard of the viewer of the digital display with an area of interest of media displayed by the digital display. Embodiments may also include receiving a myopia protocol. In some embodiments, the myopia protocol includes at least a visual blurring function. Embodiments may also include applying a visual blurring function to at least a portion of the area of interest of media displayed by the digital display.

In some embodiments, the computer program product, may include testing a visual acuity of the viewer to the applied area of interest. In some embodiments, the visual blurring function may include a contrast sensitivity function (CSF) indicative of a visual acuity field of the viewer. Embodiments may also include a contrast sensitivity function (CSF) indicative of a visual acuity of the viewer may include data indicative of a near-sightedness performance to the contrast function sensitivity performance.

Embodiments may also include a contrast sensitivity function (CSF) indicative of a visual acuity of the viewer may include a mathematical function for a Visual Blurring Function (VBF) as a function of time. In some embodiments, the mathematical function may include at least one variable for each of a treatment function for each eye of the viewer. Embodiments may also include a two-dimensional boundary of a Point of Regard for each eye of the viewer. Embodiments may also include a distance between at least one eye of the viewer and the two-dimensional boundary of the area of focus for at least one eye of the viewer.

In some embodiments, the computer program product may include rendering a first two-dimensional treatment area in a two-dimensional boundary of a Point of Regard for each eye of the viewer based at least in part on the mathematical function at time t0 and a distance between the viewer and the digital display. Embodiments may also include displaying the rendering of the first two-dimensional treatment area in the two-dimensional boundary of a Point of Regard for each eye of the viewer. Embodiments may also include determining a visual acuity field for each eye of the viewer in response to the displayed rendering of the first treatment area for each eye of the viewer at time t0 and the distance between the viewer and the digital display.

Embodiments may also include a contrast sensitivity function (CSF) indicative of a visual acuity of the viewer may include data indicative of a performance of a spatial frequency sensitivity performance. Embodiments may also include a contrast sensitivity function (CSF) indicative of a visual acuity of the viewer may include a function indicative of a visual acuity performance of the user at a distance from the digital display and its minimal Spatial Frequency Threshold for a trackable object on the digital display.

Embodiments may also include receiving a visual blurring function of the viewer may include receiving viewer digital identification data indicative of the viewer. Embodiments may also include transmitting a request for a visual acuity profile of the viewer. Embodiments may also include receiving the visual acuity profile. In some embodiments, the visual acuity profile includes at least the visual blurring function of the viewer.

Embodiments may also include receiving the visual acuity profile may include an amblyopic eye classification for each eye of the viewer. Embodiments may also include receiving a visual blurring kernel of the viewer may include receiving a contrast sensitivity function (CSF). In some embodiments, the contrast sensitivity function (CSF) may include at least one instruction for determining the spatial blurring attribute based at least in part on one or more visual acuity fields of the viewer.

In some embodiments, the computer program product may include comparing the visual acuity performance for each eye of the viewer at time t0 with a historical visual acuity performance for each eye of the viewer. Embodiments may also include updating the visual blurring function for at least one eye of the viewer if the comparison indicates a change in the visual acuity performance for the at least one eye.

Embodiments may also include at least one instruction for determining the spatial blurring attribute based at least in part on one or more visual acuity field of the viewer, the one or more visual acuity field may include at least one of a foveal visual acuity field. Embodiments may also include a paraoveal visual acuity field. Embodiments may also include a peripheral visual acuity field.

In some embodiments, the computer program product may include displaying the count of images for each eye of the viewer based on the received visual blurring kernel of the viewer. Embodiments may also include displaying the count of images for each eye of the viewer based on the received visual blurring kernel of the viewer may include dynamically altering the spatial blurring attribute for the count of images for each eye of the viewer as a function of time.

Embodiments may also include dynamically altering the spatial blurring attribute for the count of images for each eye of the viewer as a function of time may include altering the dimensions of the area of the spatial blurring attribute within the foveal visual acuity field of an eye of the viewer as a function of time. Embodiments may also include dynamically altering the spatial blurring attribute for the count of images for each eye of the viewer as a function of time may include altering the dimensions of the area of the spatial blurring attribute within the foveal visual acuity field of an eye of the viewer as a sinusoidal function of time.

Embodiments may also include dynamically altering the spatial blurring attribute for the count of images for each eye of the viewer as a function of time may include altering the dimensions of the area of the spatial blurring attribute within the foveal visual acuity field of an eye of the viewer. In some embodiments, altering the dimensions of the area of the spatial blurring attribute to maintain a cognitive load.

Embodiments may also include altering the dimensions of the area of the spatial blurring attribute to maintain a cognitive load may include inferring the cognitive load from the eye tracking information. Embodiments may also include applying a visual blurring function to at least a portion of the area of interest of media displayed by the digital display may include determining a count of images to be displayed based at least in part on one or more of a refresh rate of the digital display, a defined segment of video, a sampling rate of at least one camera of the digital display, and the visual blurring function for each eye of the viewer.

In some embodiments, the computer program product may include determining an image attribute for the count of images for each eye of the viewer based on the received visual blurring kernel of the viewer. Embodiments may also include determining an image attribute for the count of images for each eye of the viewer based on the received visual blurring kernel of the viewer may include using the eye tracking information to determine an area of interest of the digital display. Embodiments may also include correlating the area of interest of the digital display to the count of images and the distribution of projections for each eye of the viewer. Embodiments may also include applying the visual blurring kernel of the viewer to an area of interest of a projected image for at least one eye of the viewer. Embodiments may also include applying the visual blurring function of the viewer to an area of interest of a projected image for the at least one eye of the viewer may include spatially-adjusting the area of interest of the projected image for at least one eye.

DETAILED DESCRIPTION

Embodiments of the present disclosure include the administration of a myopia protocol using a digital display.

Figure 1A:
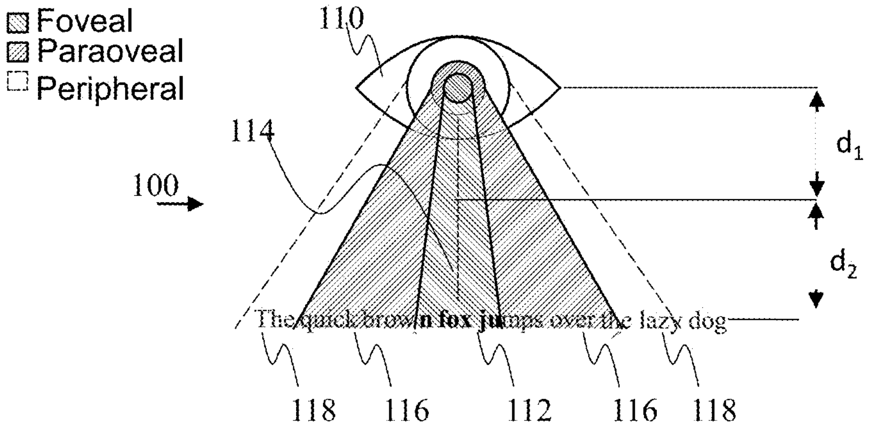
FIG. 1A is a schematic diagram depicting a visual acuity field within the point of regard of a viewer's eye, according to some embodiments of the present disclosure.

FIG. 1A is a schematic diagram depicting a visual acuity field 100 within the point of regard of a viewer's eye 110. As displayed, the visual acuity field 100 includes three regions. The first region, the foveal region 112 is a region where the visual acuity of the eye is greatest. The foveal region 112 is generally the volume defined by a 2-degree ray as measured from a center line 114 from the viewer's eye 110. The visual acuity of the viewer's eye 110 decreases further within the paraoveal field of view 116 as compared to the visual acuity within the foveal field of view 112. The paraoveal field of view 116 extends about 5 degrees from the center, while the peripheral field of view 118 extends nearly 90 degrees. The area within the field of view corresponding to a region depends on how far the object of interest is away from the viewer eye 110. For example, the area within the field of view increases from the area at $d_1$ to the area within the field of view at $d_2$. The area of focus varies as the square of the distance. For example, the area divided by the square of the distance is constant and is called the solid angle. In some embodiments, the solid angle may be measured in units of steradians (sr). The foveal region has a 3.8 millisteradian (msr) solid angle, the foveal plus parafoveal regions comprise 24 msr, and the foveal, parafoveal plus peripheral regions have a 27L sr solid angle.

In some embodiments, the regions of visual acuity may enhance the performance of a computer program product for administering a myopia protocol.

Myopia protocols, as used in the context of the described digital display system, embody a wide range of processes designed to effectively manage the progression of myopia. These protocols are not restricted to traditional treatment methods but encompass a broader scope of applications, including diagnosis, treatment administration, efficacy assessment, and treatment optimization. They may function independently or in tandem with conventional myopia protocols, providing the flexibility to cater to diverse patient needs and responses. For example, a myopia protocol may involve diagnosis procedures that utilize advanced eye tracking and image data. Treatment protocols may apply personalized blurring functions integrated with digital content rendering. Effectiveness assessment may use real-time gaze and distance monitoring, while optimization of the protocol may leverage the viewer's response and compliance data, enabling continuous refinement of the treatment approach. The adaptability of these myopia protocols underscores their potential for more personalized and effective myopia management.

Figure 1B:
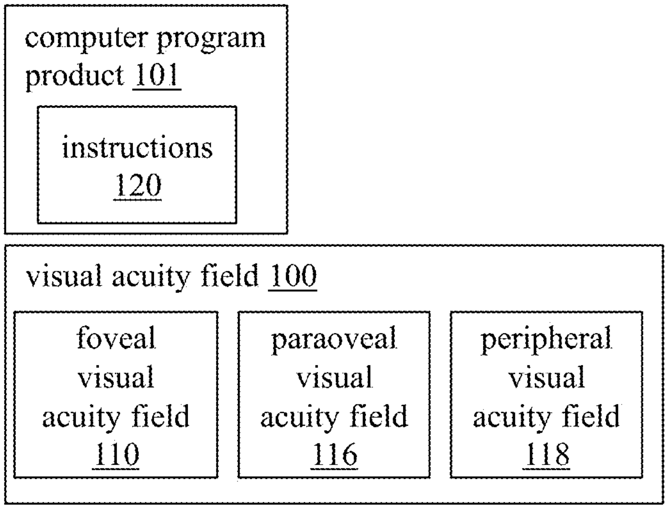
FIG. 1B a block diagram of the computer program product, according to some embodiments of the present disclosure.

Referring now to FIG. 1B, a block diagram of the computer program product 101 is depicted. In some embodiments, the computer program product 101 includes instructions 120 for using a 3D display and associated peripheral devices (e.g., a keyboard, cameras, network attached storage, media player) for the diagnosis and/or treatment of myopia of a viewer. Instruction 120 may include steps for the receiving a visual blurring kernel of the viewer. In some embodiments, the visual blurring kernel may include instructions for receiving a contrast sensitivity function (CSF). The contrast sensitivity function (CSF) may include at least one instruction for determining the spatial blurring attribute based at least in part on the acuity field of view 100 of the viewer. The visual acuity field 100 may include a foveal visual acuity field 110, a paraoveal visual acuity field 116, and a peripheral visual acuity field 118.

In some embodiments, the instructions 120 may include operations for obtaining eye landmark image data. In some embodiments, eye landmark image data may include at least one of pupil image data, iris image data, or eyeball image data. In some embodiments, a gaze angle may include at least one of yaw or pitch. In some embodiments, the instructions 120 may include operations for analyzing the eye landmark image data. The analysis of the eye landmark image data may include analyzing at least one eye state characteristic. In some embodiments, the eye state characteristic may include an assessment of at least one of a blink, an open state, or a closed state. Instructions 120 may include operations for further characterizing open states as dwells or fixations, or saccades (periods of movement of the eye from one point to another point).

In some embodiments, instructions 120 may include operations for the acquiring eye landmark image data may be performed by a camera at a distance of at least 0.2 meters from the plurality of viewers. In some embodiments, the acquiring eye landmark image data may be performed by a consumer electronics device, such as a laptop camera, tablet camera, a smartphone camera, or a digital gaming system. In some embodiments, the instructions 120 may include operations for acquiring eye landmark image data with or without active illumination of the viewer.

In some embodiments, the instructions 120 may include operations for analyzing the eye landmark image data to determine at least one eye position in three-dimensional space, at least one gaze angle, and at least one point-of-regard for at least one viewer relative to at least one camera associated with the digital display may include mapping the eye landmark image data to a Cartesian coordinate system. Embodiments instructions 120 may include operations for unprojecting the pupil and limbus of both eyeballs onto the Cartesian coordinate system to determine the three-dimensional contours of each eyeball.

In some embodiments, the instructions 120 may include operations for detecting degradation in the eye landmark image data. Embodiments comprising multiple cameras where the viewer is in the field of view, the instructions 120 may include operations for switching to a different camera having better eye landmark image data based on the detection of degradation in the eye landmark image data. In some embodiments, the instructions 120 may include operations for analyzing the eye landmark image data for at least one of engagement with the digital display, fixation, or saccade. In some embodiments, the instructions 120 may include operations for assigning a unique digital identifier to each viewer's face.

Figure 2:
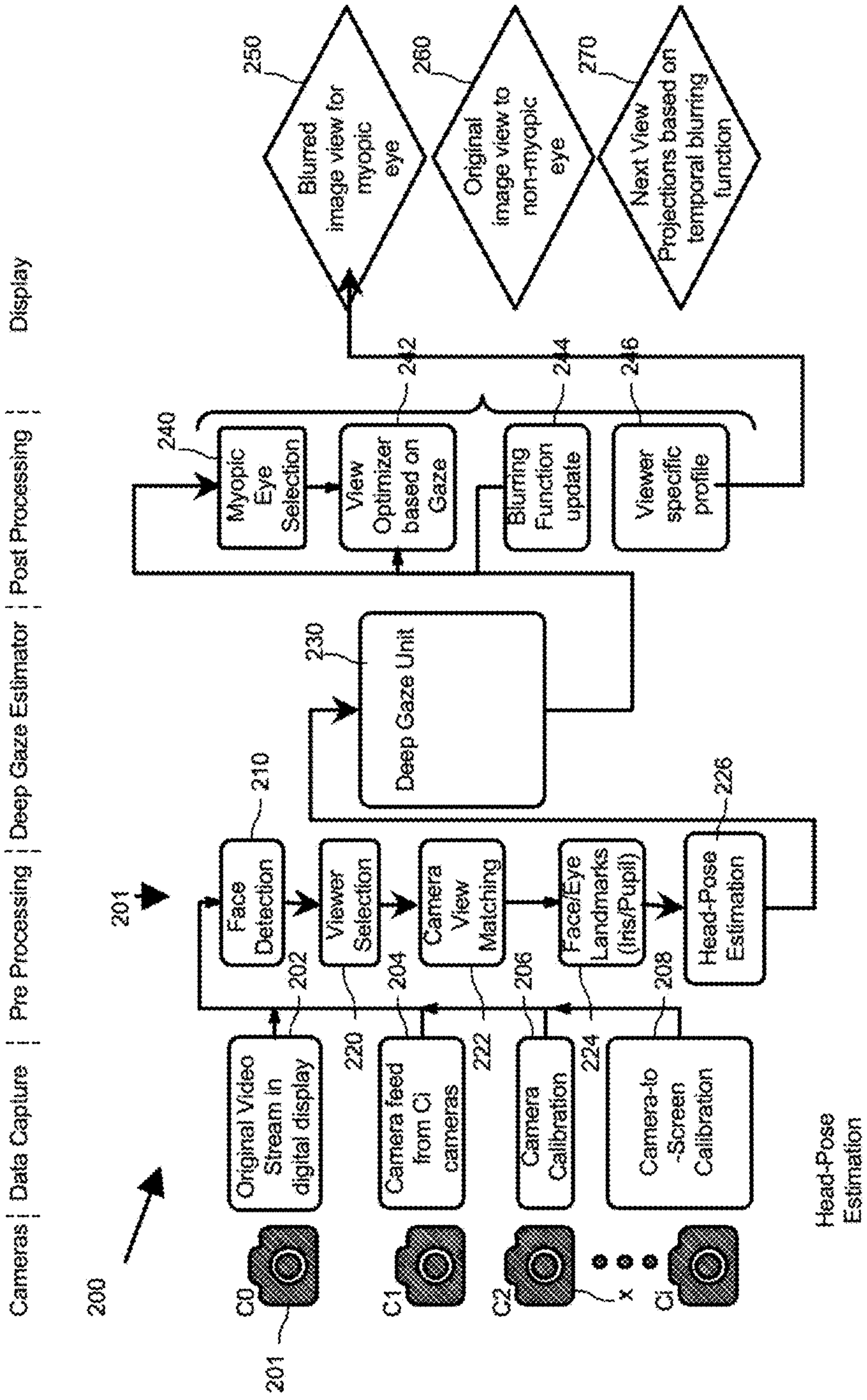
FIG. 2 is a flowchart extending from FIG. 1B and further illustrating the method for modifying digital media to be displayed on a digital display, according to some embodiments of the present disclosure.

Referring now to FIG. 2, an exemplary system flow 200 is depicted. The system flow 200 may accept image data from the camera feed 204 from cameras 201 (e.g., $C_0$, $C_1$, $C_2$ . . . $C_i$). One or more cameras 201 may support a camera calibration flow 206. The camera calibration flow 206 may include image data that can be used to identify the viewer within the field of view, a distance of the user to the camera, a sensor check of the image sensor (e.g., the camera 201 CMOS sensor), or a system control check to send and receive instructions to and from the cameras 201. A camera-to-screen calibration 208 may also be performed to calibrate the six degrees of freedom between the camera and 3D display. The image data from camera feeds 204 are processed to determine facial features of the viewer at face detection 210 of the image data pre-processing flow.

In some embodiments, additional image data pre-processing steps may be conducted to reduce the data processing burden of the CPU and/or GPU of the deep gaze unit 230. A graphical user interface may be used to support a viewer selection 220 to initiate an myopia protocol. In some embodiments, recognition of one or more of face/eye landmarks 224 may support a matching function of previous viewers with the viewer in the field of view of the cameras 201. Additional image data processing across multiple cameras 201 may be used to match views within each of the camera field of views. Image data processing may also be performed to identify facial landmarks 224 and head-pose estimation 226.

In some embodiments, the deep gaze unit 230 may support key functions in the treatment of myopia including determining eye localization, eye state, fixation, saccade, and gaze estimation. Post processing steps 240, 242, 244, and 246 may collectively be used to apply a blurring function to the original video stream 202 to provide a myopia treatment that is customized to the individual viewer. In some embodiments, the myopic eye is selected based on the loaded viewer specific profile 246. The blurring function will be applied to the pixels correlated with the viewer's point-of-regard. In some embodiments, as the treatment progresses, a blurring function update 244 may be implemented.

In some embodiments, the updated image view is displayed with a blurred image view for the myopic eye 250 and an original image view to the other eye 260. The display functions may also receive the next view projections and begin processing the images based on the temporal blurring function 270 for presentation to the viewer's eyes 250 and 260.

In some embodiments, a mathematical function for a Visual Blurring Function (VBF) as a function of time may be represented as follows:

$$f_{blur}(d, vfov, t) = A \cdot |\sin(\alpha\pi t)| \cdot \begin{Bmatrix} K_{foveal} & vfov \in \text{foveal}(d) \\ K_{parafoveal} & vfov \in \text{parafoveal} \\ K_{peripheral} & vfov \in \text{peripheral} \end{Bmatrix}$$

$t$ = temporal interval, $d$ = distance to *scrteen*, $vfov$ = visual field of view, -continued $$A - \text{blureing Amplitude}, |.| = \text{absolute value operator}$$

$$K_{peripheral} = \begin{cases} \begin{bmatrix} k_{diag} & k(nDiag) & k_{diag} \\ k(nDiag) & k(\text{center}) & k(nDiag) \\ k_{diag} & k(nDiag) & k_{diag} \end{bmatrix} & \alpha t \notin \mathbb{Z} \\ I_{3\times 3} & \text{else} \end{cases}$$

$$K_{parafoveal} = \begin{cases} \begin{bmatrix} \frac{k_{diag}}{2} & \frac{k_{nDiag}}{2} & \frac{k_{nDiag}}{2} & \frac{k_{nDiag}}{2} & \frac{k_{diag}}{2} \\ \frac{k_{nDiag}}{2} & k_{diag} & k_{nDiag} & k_{diag} & \frac{k_{nDiag}}{2} \\ \frac{k_{nDiag}}{2} & k_{nDiag} & k(\text{center}) & k_{nDiag} & \frac{k_{nDiag}}{2} \\ \frac{k_{nDiag}}{2} & k_{diag} & k_{nDiag} & k_{diag} & \frac{k_{nDiag}}{2} \\ \frac{k_{diag}}{2} & \frac{k_{nDiag}}{2} & \frac{k_{nDiag}}{2} & \frac{k_{nDiag}}{2} & \frac{k_{diag}}{2} \end{bmatrix} & \alpha t \notin \mathbb{Z} \\ I_{5\times 5} & \text{else} \end{cases}$$

$$K_{foveal} =$$

$$\begin{cases} \begin{bmatrix} \frac{k_{diag}}{4} & \frac{k_{nDiag}}{4} & \frac{k_{nDiag}}{4} & \frac{k_{nDiag}}{4} & \frac{k_{nDiag}}{4} & \frac{k_{nDiag}}{4} & \frac{k_{diag}}{4} \\ \frac{k_{nDiag}}{4} & \frac{k_{diag}}{2} & \frac{k_{nDiag}}{2} & \frac{k_{nDiag}}{2} & \frac{k_{nDiag}}{2} & \frac{k_{diag}}{2} & \frac{k_{nDiag}}{4} \\ \frac{k_{nDiag}}{4} & \frac{k_{nDiag}}{2} & k_{diag} & k_{nDiag} & k_{diag} & \frac{k_{nDiag}}{2} & \frac{k_{nDiag}}{4} \\ \frac{k_{nDiag}}{4} & \frac{k_{nDiag}}{2} & k_{nDiag} & k(\text{center}) & k_{nDiag} & \frac{k_{nDiag}}{2} & \frac{k_{nDiag}}{4} \\ \frac{k_{nDiag}}{4} & \frac{k_{nDiag}}{2} & k_{diag} & k_{nDiag} & k_{diag} & \frac{k_{nDiag}}{2} & \frac{k_{nDiag}}{4} \\ \frac{k_{nDiag}}{4} & \frac{k_{diag}}{2} & \frac{k_{nDiag}}{2} & \frac{k_{nDiag}}{2} & \frac{k_{nDiag}}{2} & \frac{k_{diag}}{2} & \frac{k_{nDiag}}{4} \\ \frac{k_{diag}}{4} & \frac{k_{nDiag}}{4} & \frac{k_{nDiag}}{4} & \frac{k_{nDiag}}{4} & \frac{k_{nDiag}}{4} & \frac{k_{nDiag}}{4} & \frac{k_{diag}}{4} \end{bmatrix} & \alpha t \notin \mathbb{Z} \\ I_{7\times 7} & \text{else} \end{cases}$$

Final output for the rendering module is the 2D image projection to the user's eyes is done via an AI module, The method is using Gaze Tracking to estimate the User's point-of-regard (PoR)—which is the user's fixation on the digital-display at a specific time stamp, and uses this information, in addition to other parameters, to perform a digital peripheral blur (DPB) with high refresh rate:

$$\text{Point-Of-Regard-Group}(PORG) = \{\text{foveal}(d), \text{parafoveal}(d), \text{peripheral}(d)\}$$

$$\text{Image}_{MyopicTreatment}(X, Y) = \begin{cases} \text{Image}_{Original}(X, Y) & X, Y \in PORG \\ \text{Image}_{Original}(X, Y) * f_{blur}(d, vfov, t) & \text{otherwise} \end{cases}$$

$$(X, Y)\text{-pixel location in the image plane,}$$

$$*\text{-is the } 2D \text{ covolution operation}$$

$$\text{Image}_{Original} = \text{the original content digital image } presneted \text{ on the digital } dispaly$$

Additionally, further examples of a mathematical function for a Visual Blurring Function (VBF) as a function of time are disclosed with respect to 3D displays in the U.S. non-provisional utility patent application Ser. No. 18/123,280 owned by the present Applicant entitled "SYSTEM AND METHOD FOR THE DIAGNOSIS AND TREATMENT OF AMBLYOPIA USING A 3D DISPLAY," the contents of which are incorporated in their entirety to the extent they are not inconsistent with the present disclosure.

Figure 3:
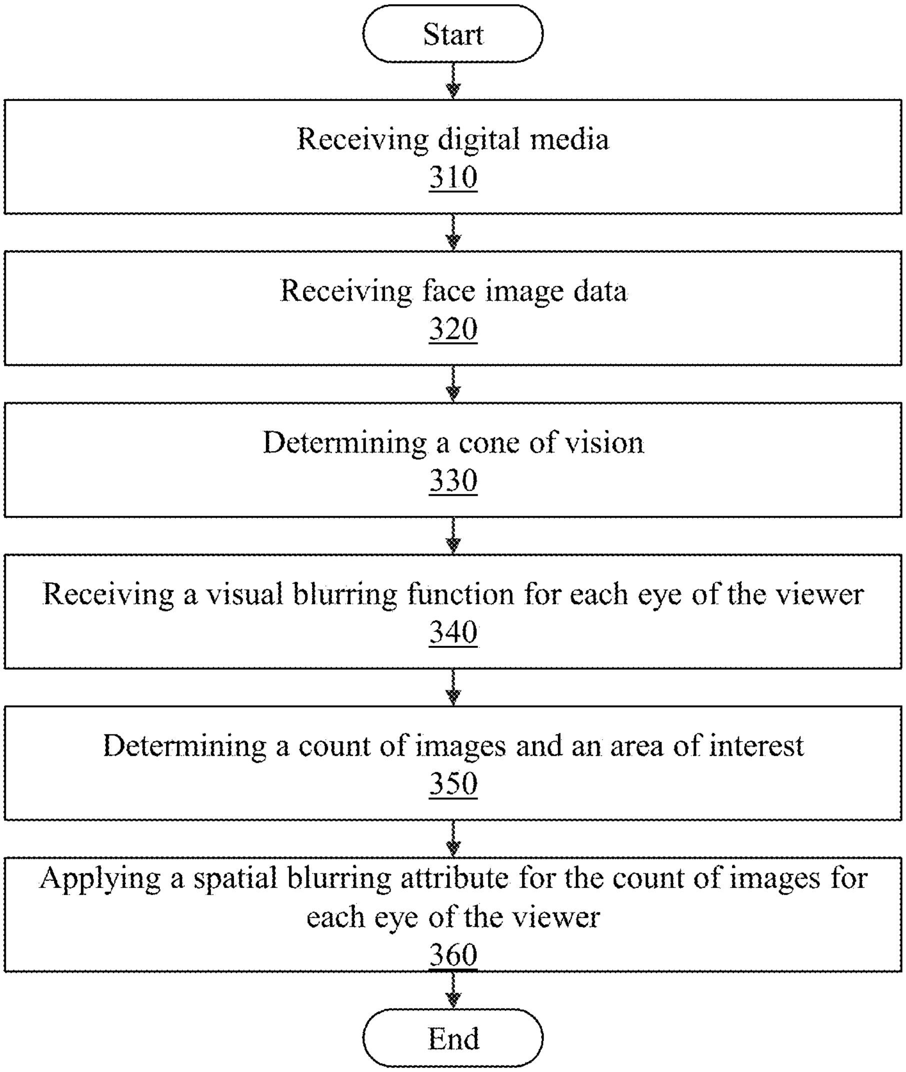
FIG. 3 is a flowchart illustrating a method for modifying digital media to be displayed on a digital display, according to some embodiments of the present disclosure.

FIG. 3 is a flowchart that describes a method for modifying digital media to be displayed on a digital display, according to some embodiments of the present disclosure. In some embodiments, digital media may include movies, TV shows, web series, live streams, video blogs (vlogs), tutorials, and the like. Video content is available through various platforms like Netflix, YouTube, Hulu, Amazon Prime Video, and others. In some embodiments, at 310, the method may include receiving digital media. In some embodiments, the digital media may be received at a digital display adapted to modify received digital media based on a myopia protocol. In an alternative embodiment, consumer electronics may be augmented by installing a myopia protocol application, such as applications purchased from application stores, like the Apple App Store. At 320, the method may include receiving face image data, eye landmark image data for a viewer within a field of view of at least one camera in proximity to a viewer, and a distance between the digital display and the viewer. At 330, the method may include determining a cone of vision. Such information may be used to apply a blurring function to an area of interest within the displayed media on the digital display. At 340, the method may include receiving a visual blurring function for each eye of the viewer. The method 340 may be automated by associating the visual blurring function with login credentials used by the viewer of the digital display.

In some embodiments, at 350, the method may include determining a count of images and an area of interest within the boundaries of a frame of each image. In some embodiments the area of interest is based at least in part on the eye tracking information. Eye tracking information may be used to identify an area of interest correlated with the area of fixation. At 360, the method may include applying a spatial blurring attribute for the count of images for each eye of the viewer based at least in part on the received visual blurring function of the viewer, the determined area of interest, and the myopia protocol. The count of images in some embodiments may be based on an appropriate sampling rate. An appropriate sampling rate may be based on a refresh rate of the digital display, for example a display having at least a 2 k refresh rate. In some embodiments, the count of images may be based on a quantified period of fixation of the viewer, for example a minimum period between gaze drift. Alternatively, transition periods within the digital media may be monitored for scene breaks, changes in camera orientation, or changes in the expected focal point of an image. In such instances, the count may be used as the basis for the application of the spatial blurring attribute. For example, the spatial blurring function may be applied based on a myopia protocol that is applied as a function of time when the contents of subsequent images are appropriate for blurring. The gaze direction, the cone of vision, and distance between the digital display and the viewer may be used to infer a region of fixation while the count may be used to ensure the quality of the administered myopia protocol.

In some embodiments, the myopia diagnosis protocol may be based at least in part on a visual acuity test, a refraction test, a retinoscopy, an autorefractor, and a dilated eye exam. In some embodiments, the myopia treatment protocol may further comprise use of prescription eyeglasses, prescription contact lenses, and an orthokeratology. In some embodiments, the myopia treatment protocol may further comprise use of prescription eyeglasses, prescription contact lenses, and an orthokeratology outside of a viewing session. The modified digital media may be displayed on the digital display.

In some embodiments, an aspect of the quality of the treatment protocol includes associating at least one parameter relevant to the quality of the myopia protocol with a viewer profile. These parameters can significantly vary, encompassing aspects such as a current visual acuity measurement of the viewer. Such a visual acuity measurement may provide an accurate baseline of the viewer's vision or a predicted myopic assessment of the viewer prior to initiating the myopia protocol. The visual acuity measurement may also include an indicator representing the progression status of a myopia condition, providing key eye health data on either the disease's advancement or stabilization. Aspects like an eye health examination offer comprehensive insights into the overall ocular health of the viewer and may be associated with the viewer's profile. Compliance parameters can track the viewer's adherence to the treatment protocol and may be used uncover a causal effect between the myopia protocol and quality of care over time. The parameters of the viewer profile may also involve a myopia treatment prescription, outlining the specific treatment plan for the viewer. A session performance value could also be considered, offering feedback on the effectiveness of each treatment session. In some embodiments, the specific treatment plans of multiple viewers may be aggregated into cohorts of patients with similar myopic conditions, viewer behaviors, responses to treatment/monitoring protocols, and/or age groups. In some embodiments, artificial intelligence may be used to fine tune myopia protocols being administered to patients. In some embodiments, the method may involve performing one or more additional steps based on the results of the analysis of cohort data.

In some embodiments, receiving digital media further comprises receiving at a processor digital media from at least one of a streaming service, a dedicated media device, a video gaming console, an online gaming service, a social media site, and a live streaming service. In some embodiments, the digital media may be at least one of a podcast, a social media post, a live streaming event, a video game, a webpage, an e-book, a video call, augmented reality information, and a virtual reality environment.

In some embodiments, the digital media may be at least one of a still image, a video, a movie, a television program, a social media content, and specialized content for the treatment of myopia. In some embodiments, receiving digital media further comprises receiving the digital media at a processor via one or more of a wireless streaming service, a connected media player, a connected laptop, a connected remote server, and a local server.

In some embodiments, a contrast sensitivity function (CSF) indicative of a visual acuity of the viewer further comprises, the method may include performing one or more additional steps. Data indicative of a performance of a contrast function sensitivity performance. In some embodiments, a contrast sensitivity function (CSF) indicative of a visual acuity of the viewer further comprises, the method may include performing one or more additional steps. Data indicative of a performance of a spatial frequency sensitivity performance.

In some embodiments, a contrast sensitivity function (CSF) indicative of a visual acuity of the viewer further comprises, the method may include performing one or more additional steps. A function indicative of a visual acuity performance of the user at a distance from the digital display and its minimal Spatial Frequency Threshold for a trackable object on the digital display. In some embodiments, receiving the visual acuity profile may further comprise a myopia assessment for each eye of the viewer.

In some embodiments, receiving a visual blurring function of the viewer further comprises, the method may include performing one or more additional steps. The contrast sensitivity function (CSF) further may comprise at least one instruction for applying the spatial blurring attribute based at least in part on the received visual blurring function of the viewer and the myopia protocol. In some embodiments, applying a spatial blurring attribute for the count of images for each eye of the viewer based at least in part on the received visual blurring function of the viewer and the myopia protocol further comprises at least one instruction for determining the spatial blurring attribute for the count of images for each eye of the viewer based at least in part on one or more visual acuity fields of the viewer, the one or more visual acuity field. The visual acuity field further comprises at least one of, the method may include performing one or more additional steps. A foveal visual acuity field. A parafoveal visual acuity field. A peripheral visual acuity field. In some embodiments, applying a spatial blurring attribute for the count of images for each eye of the viewer based at least in part on the received visual blurring function of the viewer and the myopia protocol further comprises, the method may include performing one or more additional steps.

Figure 4A:
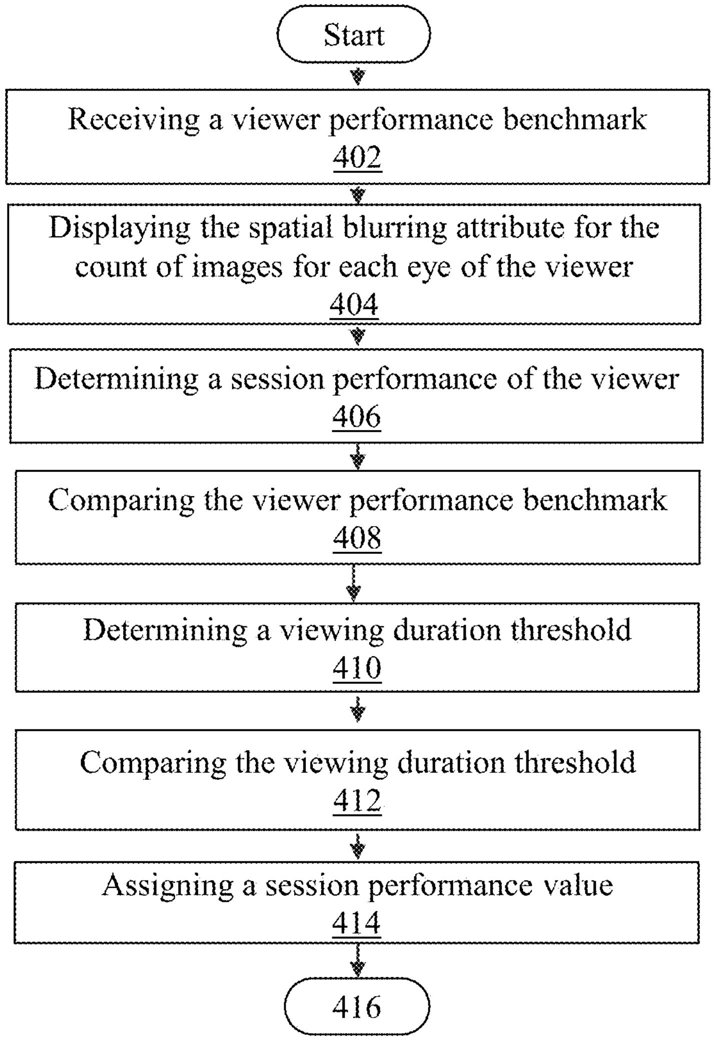
FIG. 4A is a flowchart further illustrating the method for modifying digital media to be displayed on a digital display from FIG. 3, according to some embodiments of the present disclosure.
Figure 4B:
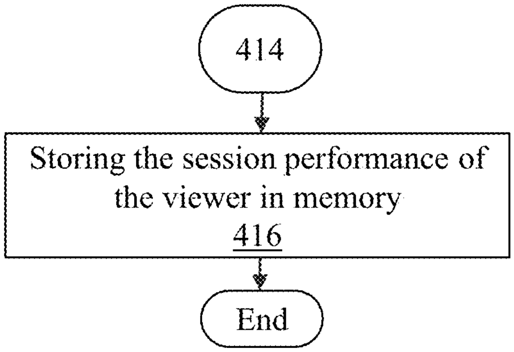
FIG. 4B is a flowchart extending from FIG. 4A and further illustrating the method for modifying digital media to be displayed on a digital display, according to some embodiments of the present disclosure.

FIGS. 4A to 4B are flowcharts that further describe the method for modifying digital media to be displayed on a digital display from FIG. 3, according to some embodiments of the present disclosure. In some embodiments, the myopia protocol may be at least one of a myopia diagnosis protocol, a myopia treatment protocol, and a quality of treatment protocol. In some embodiments, the quality of treatment protocol further comprises, the method may include 402 to 408. In some embodiments, at 410, the method may include determining a viewing duration threshold. At 412, the method may include comparing the viewing duration threshold with the viewer performance benchmark. At 414, the method may include assigning a session performance value based on the comparison. At 416, the method may include storing the session performance of the viewer in memory. The determining may be based at least in part on the duration. The inferred region of fixation may match the two-dimensional distribution of the projections for each eye of the viewer.

Figure 5:
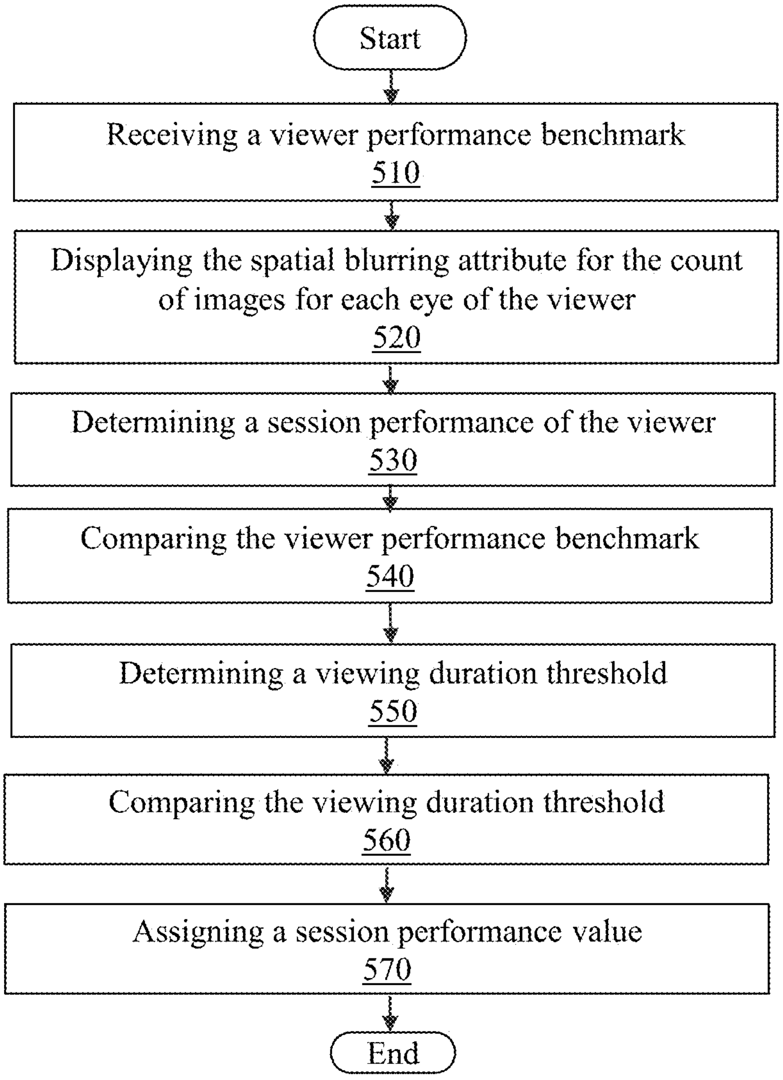
FIG. 5 is a flowchart further illustrating the method for modifying digital media to be displayed on a digital display from FIG. 3, according to some embodiments of the present disclosure.

FIG. 5 is a flowchart that further describes the method for modifying digital media to be displayed on a digital display from FIG. 3, according to some embodiments of the present disclosure. In some embodiments, the myopia protocol may be at least one of a myopia diagnosis protocol, a myopia treatment protocol, and a quality of treatment protocol. In some embodiments, the quality of treatment protocol further comprises, the method may include 402 to 408. In some embodiments, receiving a viewer performance benchmark may further comprise a minimum viewing duration threshold. In some embodiments, determining a session performance of the viewer based at least in part on the displayed spatial blurring attribute for the count of images for each eye of the viewer further comprises, the method may include 550 to 570. The determining may be based at least in part on the duration. The inferred region of fixation may match the two-dimensional distribution of the projections for each eye of the viewer.

Figure 6:
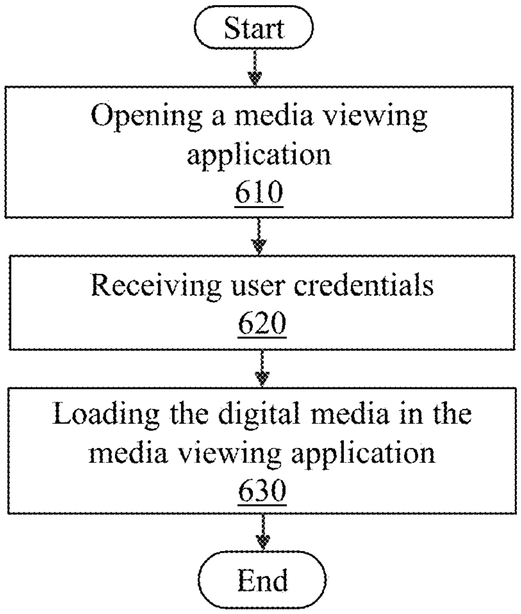
FIG. 6 is a flowchart further illustrating the method for modifying digital media to be displayed on a digital display from FIG. 3, according to some embodiments of the present disclosure.

FIG. 6 is a flowchart that further describes the method for modifying digital media to be displayed on a digital display from FIG. 3, according to some embodiments of the present disclosure. In some embodiments, receiving digital media further comprises, the method may include 610 to 630. In some embodiments, a media viewing application may be a myopia treatment application.

Figure 7:
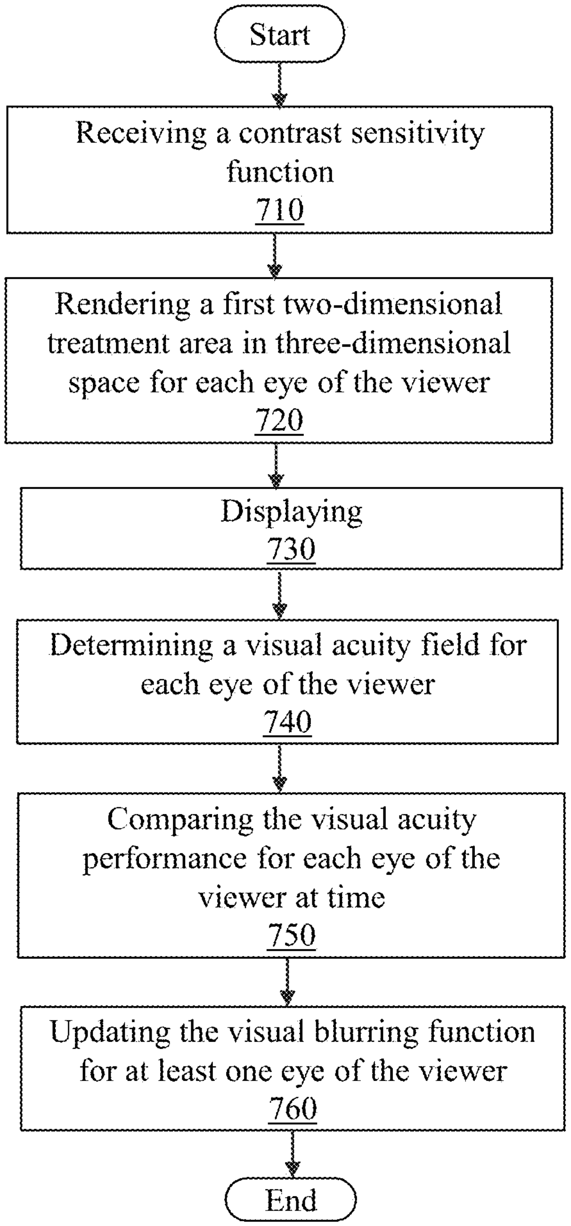
FIG. 7 is a flowchart further illustrating the method for modifying digital media to be displayed on a digital display from FIG. 3, according to some embodiments of the present disclosure.

FIG. 7 is a flowchart that further describes the method for modifying digital media to be displayed on a digital display from FIG. 3, according to some embodiments of the present disclosure. In some embodiments, receiving a visual blurring function of the viewer further comprises, the method may include 710. In some embodiments, a contrast sensitivity function (CSF) indicative of a visual acuity of the viewer further comprises, the method may include performing one or more additional steps, including applying a mathematical function for a Visual Blurring Function (VBF) as a function of time. The mathematical function further comprises at least one variable for each of, the method may include performing one or more additional steps. For example, the mathematical function may include a treatment function for each eye of the viewer, a two-dimensional boundary of a Point of Regard for each eye of the viewer, a distance between at least one eye of the viewer and the two-dimensional boundary of the area of focus for at least one eye of the viewer, and/or at least one projection.

In some embodiments, the method may include rendering a first two-dimensional treatment area for each eye of the viewer based at least in part on the mathematical function at time $t_0$. The method may include determining a visual acuity field for each eye of the viewer in response to the displayed rendering of the first treatment area for each eye of the viewer at time $t_0$. For an exemplary overview of visual acuity, see: Visual Acuity (no date) Wikipedia. Available at: https://en.wikipedia.org/wiki/Visual_acuity (Accessed: Feb. 11, 2023); hereby incorporated by reference. In some embodiments, the mathematical function for a Visual Blurring Function (VBF) may blur the two-dimensional treatment area for an eye of the viewer by applying a Gaussian Function to the pixels corresponding with the viewer's Point of Regard. In some embodiments, the mathematical function for a Visual Blurring Function (VBF) may blur the two-dimensional treatment area for an eye of the viewer by simulating a prescription/diopter perspective of the viewer.

In some embodiments, at 720, the method may include rendering a first two-dimensional treatment area for each eye of the viewer based at least in part on the mathematical function at time t0. At 730, the method may include displaying the rendering of the first two-dimensional treatment area for each eye of the viewer. At 740, the method may include determining a visual acuity field for each eye of the viewer in response to the displayed rendering of the first treatment area for each eye of the viewer at time t0.

In some embodiments, at 750, the method may include comparing the visual acuity performance for each eye of the viewer at time t0 with a historical visual acuity performance for each eye of the viewer. At 760, the method may include updating the visual blurring function for at least one eye of the viewer if the comparison indicates a change in the visual acuity performance for at least one eye. In some embodiments, the updating the visual blurring function for at least one eye of the viewer if the comparison may indicate a change in the visual acuity performance for the at least one eye, the change in visual acuity further comprises at least one of an indication of an improvement in visual acuity and a deterioration in visual acuity.

Figure 8:
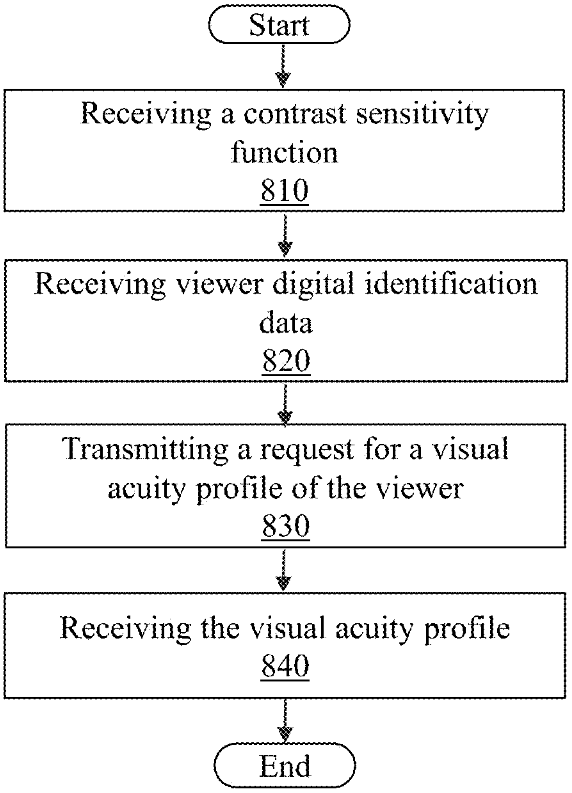
FIG. 8 is a flowchart further illustrating the method for modifying digital media to be displayed on a digital display from FIG. 3, according to some embodiments of the present disclosure.

FIG. 8 is a flowchart that further describes the method for modifying digital media to be displayed on a digital display from FIG. 3, according to some embodiments of the present disclosure. In some embodiments, receiving a visual blurring function of the viewer further comprises, the method may include 710. In some embodiments, receiving a visual blurring function of the viewer further comprises, the method may include 820 to 840. The visual acuity profile may include at least the visual blurring function of the viewer and a myopia treatment protocol.

Figure 9:
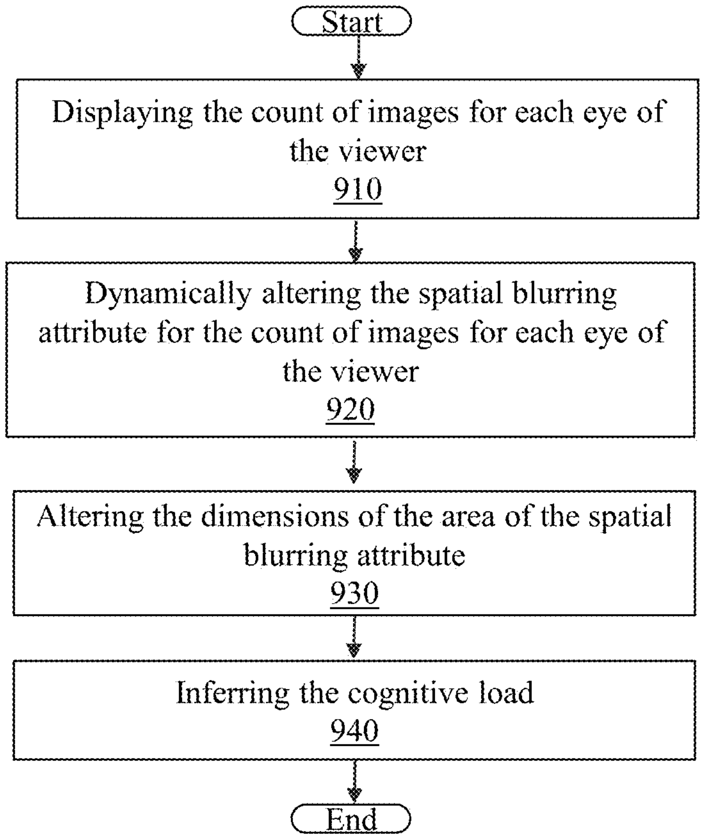
FIG. 9 is a flowchart further illustrating the method for modifying digital media to be displayed on a digital display from FIG. 3, according to some embodiments of the present disclosure.

FIG. 9 is a flowchart that further describes the method for modifying digital media to be displayed on a digital display from FIG. 3, according to some embodiments of the present disclosure. In some embodiments, at 910, the method may include displaying the count of images for each eye of the viewer based on the received visual blurring function of the viewer. In some embodiments, displaying the count of images for each eye of the viewer based on the received visual blurring function of the viewer further comprises, the method may include 920. In some embodiments, dynamically altering the spatial blurring attribute for the count of images for each eye of the viewer as a function of time further comprises, the method may include 930. In some embodiments, altering the dimensions of the area of the spatial blurring attribute to maintain a cognitive load further comprises, the method may include 940.

Figure 10:
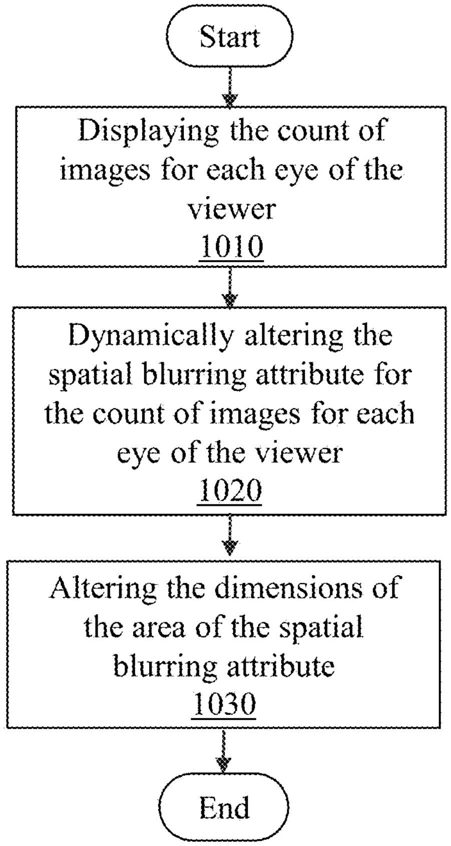
FIG. 10 is a flowchart further illustrating the method for modifying digital media to be displayed on a digital display from FIG. 3, according to some embodiments of the present disclosure.

FIG. 10 is a flowchart that further describes the method for modifying digital media to be displayed on a digital display from FIG. 3, according to some embodiments of the present disclosure. In some embodiments, at 910, the method may include displaying the count of images for each eye of the viewer based on the received visual blurring function of the viewer. In some embodiments, displaying the count of images for each eye of the viewer based on the received visual blurring function of the viewer further comprises, the method may include 920. In some embodiments, dynamically altering the spatial blurring attribute for the count of images for each eye of the viewer as a function of time further comprises, the method may include 1030.

Figure 11:
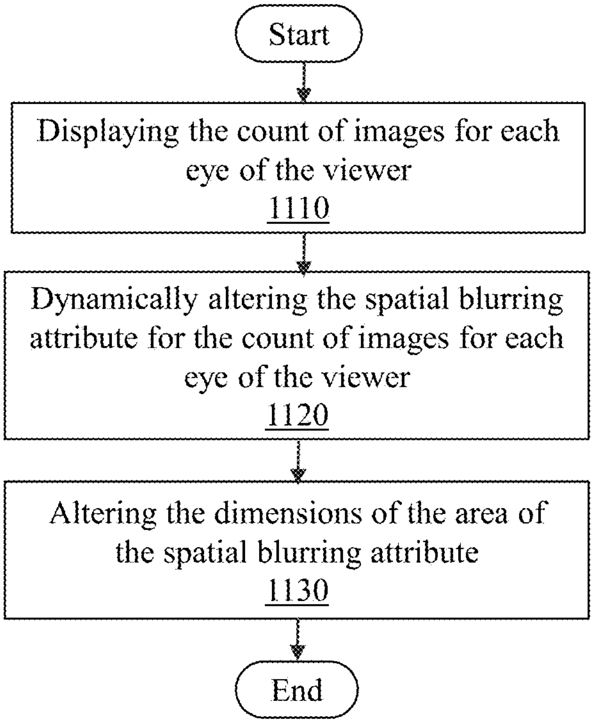
FIG. 11 is a flowchart further illustrating the method for modifying digital media to be displayed on a digital display from FIG. 3, according to some embodiments of the present disclosure.

FIG. 11 is a flowchart that further describes the method for modifying digital media to be displayed on a digital display from FIG. 3, according to some embodiments of the present disclosure. In some embodiments, at 910, the method may include displaying the count of images for each eye of the viewer based on the received visual blurring function of the viewer. In some embodiments, displaying the count of images for each eye of the viewer based on the received visual blurring function of the viewer further comprises, the method may include 920. In some embodiments, dynamically altering the spatial blurring attribute for the count of images for each eye of the viewer as a function of time further comprises, the method may include 1130. Altering the dimensions of the area of the spatial blurring attribute to maintain a cognitive load.

Figure 12:
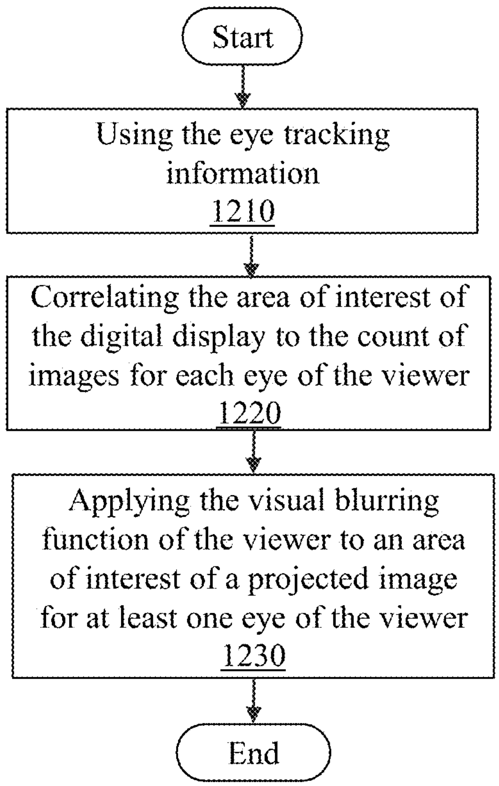
FIG. 12 is a flowchart further illustrating the method for modifying digital media to be displayed on a digital display from FIG. 3, according to some embodiments of the present disclosure.

FIG. 12 is a flowchart that further describes the method for modifying digital media to be displayed on a digital display from FIG. 3, according to some embodiments of the present disclosure. In some embodiments, applying a spatial blurring attribute for the count of images for each eye of the viewer based at least in part on the received visual blurring function of the viewer and the myopia protocol further comprises, the method may include 1210 to 1230. In some embodiments, applying the visual blurring function of the viewer to an area of interest of a projected image for the at least one eye of the viewer further comprises, the method may include performing one or more additional steps. Spatially adjusting the area of interest of the projected image for the at least one eye based at least in part on the myopia treatment protocol.

Figure 13:
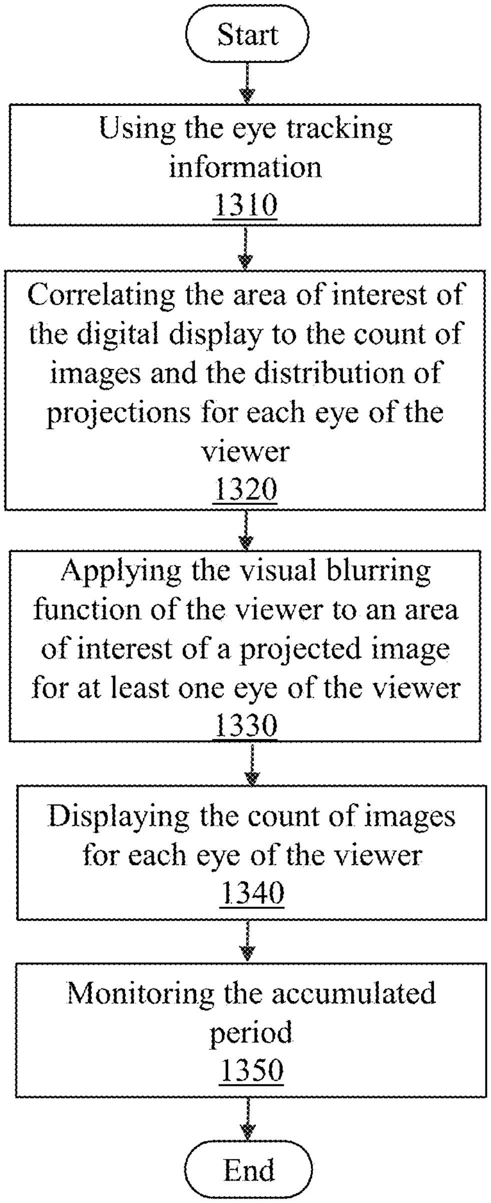
FIG. 13 is a flowchart further illustrating the method for modifying digital media to be displayed on a digital display from FIG. 3, according to some embodiments of the present disclosure.

FIG. 13 is a flowchart that further describes the method for modifying digital media to be displayed on a digital display from FIG. 3, according to some embodiments of the present disclosure. In some embodiments, at 1310, the method may include using the eye tracking information to determine an area of interest via the point-of-regard of the digital display. At 1320, the method may include correlating the area of interest of the digital display to the count of images and the distribution of projections for each eye of the viewer. At 1330, the method may include applying the visual blurring function of the viewer to an area of interest of a projected image for at least one eye of the viewer. At 1340, the method may include displaying the count of images for each eye of the viewer based on the received visual blurring function of the viewer. Spatially adjusting the area of interest of the projected image for the at least one eye.

In some embodiments, spatially adjusting the area of interest of the projected image for the at least one eye further comprises, the method may include 1350. Temporally adjusting the application of the visual blurring function of the viewer to the area of interest of the projected image for at least one eye of the viewer. The visual blurring function of the viewer may be applied to the area of interest of the projected image for at least one eye of the viewer.

Figure 14:
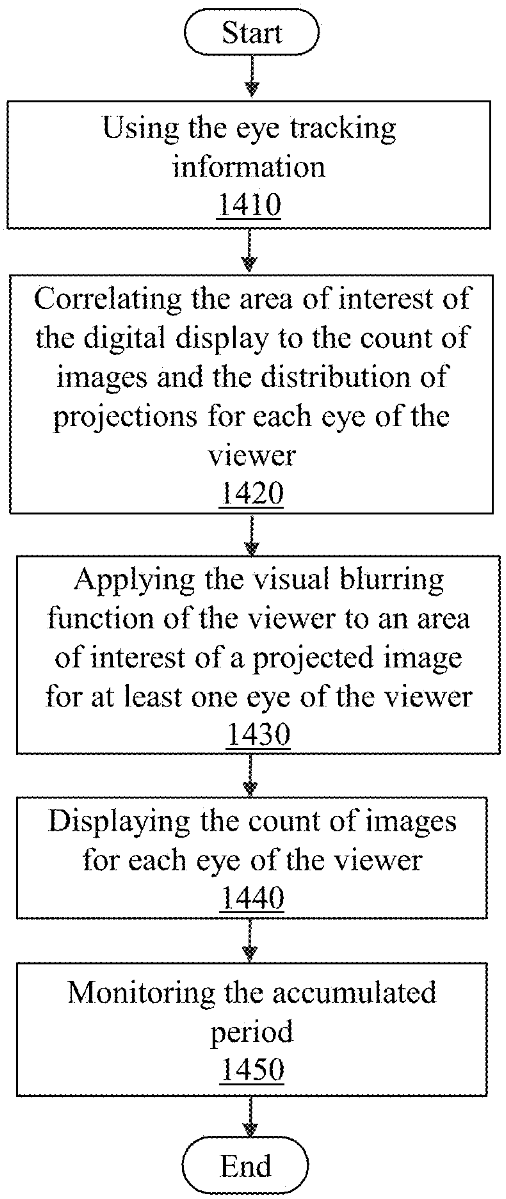
FIG. 14 is a flowchart further illustrating the method for modifying digital media to be displayed on a digital display from FIG. 3, according to some embodiments of the present disclosure.
Figure 15A:
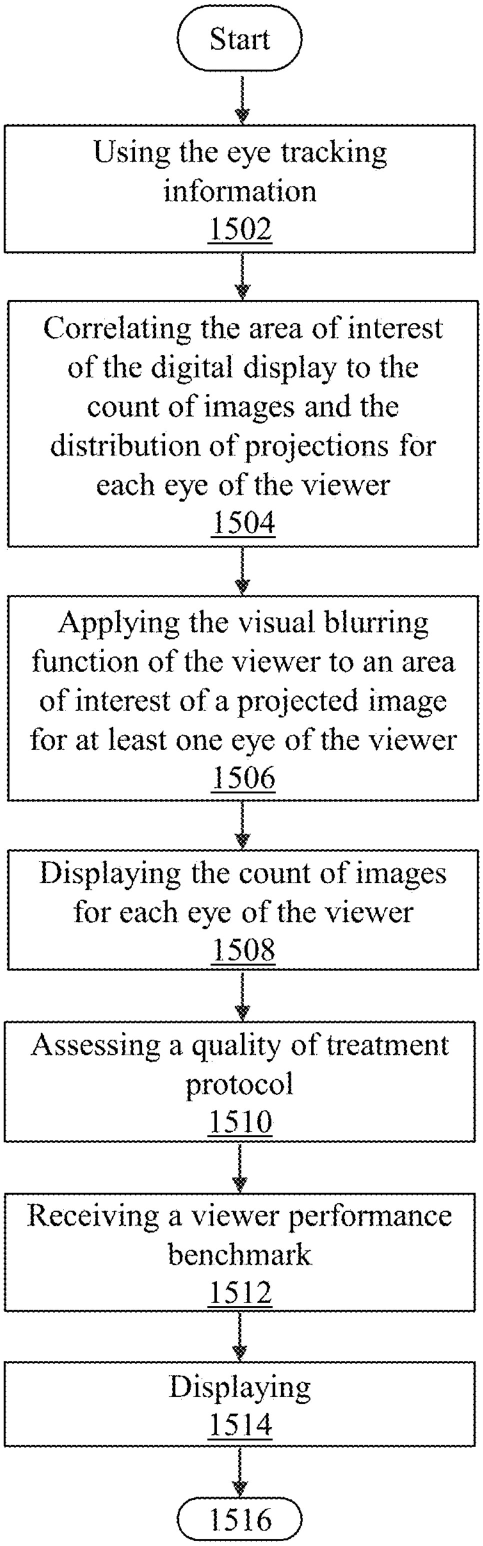
FIG. 15A is a flowchart further illustrating the method for modifying digital media to be displayed on a digital display from FIG. 3, according to some embodiments of the present disclosure.
Figure 15B:
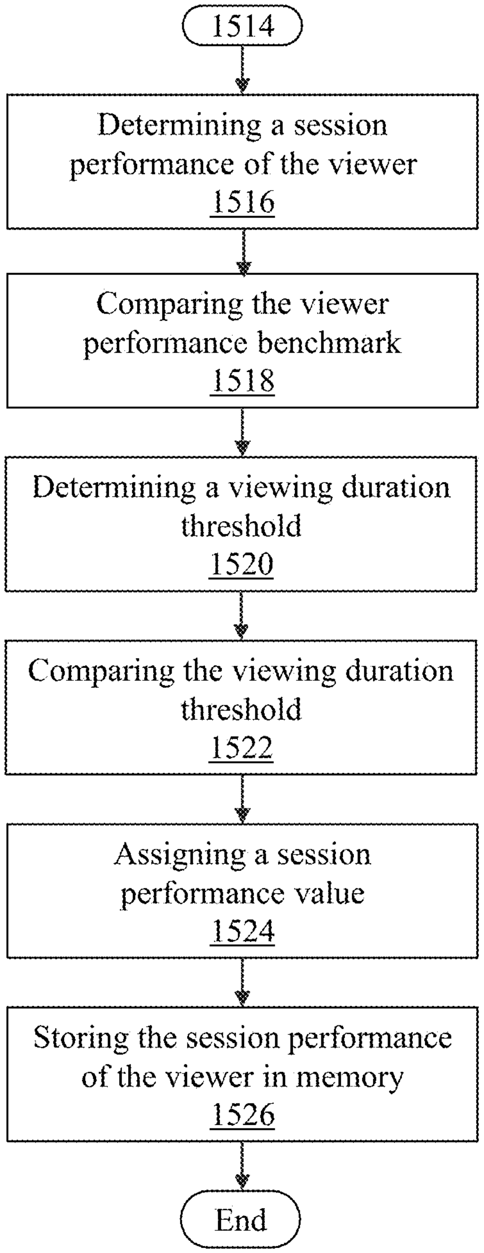
FIG. 15B is a flowchart extending from FIG. 15A and further illustrating the method for modifying digital media to be displayed on a digital display, according to some embodiments of the present disclosure.

FIG. 14 is a flowchart that further describes the method for modifying digital media to be displayed on a digital display from FIG. 3, according to some embodiments of the present disclosure. In some embodiments, at 1410, the method may include using the eye tracking information to determine an area of interest via the point-of-regard of the digital display. At 1420, the method may include correlating the area of interest of the digital display to the count of images and the distribution of projections for each eye of the viewer. At 1430, the method may include applying the visual blurring function of the viewer to an area of interest of a projected image for at least one eye of the viewer. At 1440, the method may include displaying the count of images for each eye of the viewer based on the received visual blurring function of the viewer. Temporally adjusting the area of interest of the projected image for the at least one eye. In some embodiments, at 1450, the method may include monitoring the accumulated period. The visual blurring function of the viewer may be applied to the area of interest of the projected image for at least one eye of the viewer.

FIGS. 13A to 13B are flowcharts that further describe the method for modifying digital media to be displayed on a digital display from FIG. 3, according to some embodiments of the present disclosure. In some embodiments, at 1410, the method may include using the eye tracking information to determine an area of interest via the point-of-regard of the digital display. At 1420, the method may include correlating the area of interest of the digital display to the count of images and the distribution of projections for each eye of the viewer. At 1430, the method may include applying the visual blurring function of the viewer to an area of interest of a projected image for at least one eye of the viewer. At 1440, the method may include displaying the count of images for each eye of the viewer based on the received visual blurring function of the viewer. Temporally adjusting the area of interest of the projected image for at least one eye.

In some embodiments, at 1510, the method may include assessing the quality of treatment protocol. In some embodiments, a quality of treatment protocol further comprises, the method may include 1512 to 1518. In some embodiments, at 1520, the method may include determining a viewing duration threshold. At 1522, the method may include comparing the viewing duration threshold with the viewer performance benchmark. At 1524, the method may include assigning a session performance value based on the comparison. At 1526, the method may include storing the session performance of the viewer in memory. The determining may be based at least in part on the duration. The inferred region of fixation may match the two-dimensional distribution of the projections for each eye of the viewer.

FIGS. 14A to 14B are flowcharts that further describe the method for modifying digital media to be displayed on a digital display from FIG. 3, according to some embodiments of the present disclosure. In some embodiments, at 1410, the method may include using eye tracking information to determine an area of interest via the point-of-regard of the digital display. At 1420, the method may include correlating the area of interest of the digital display to the count of images and the distribution of projections for each eye of the viewer. At 1430, the method may include applying the visual blurring function of the viewer to an area of interest of a projected image for at least one eye of the viewer. At 1440, the method may include displaying the count of images for each eye of the viewer based on the received visual blurring function of the viewer. Temporally adjusting the area of interest of the projected image for the at least one eye.

Figure 16A:
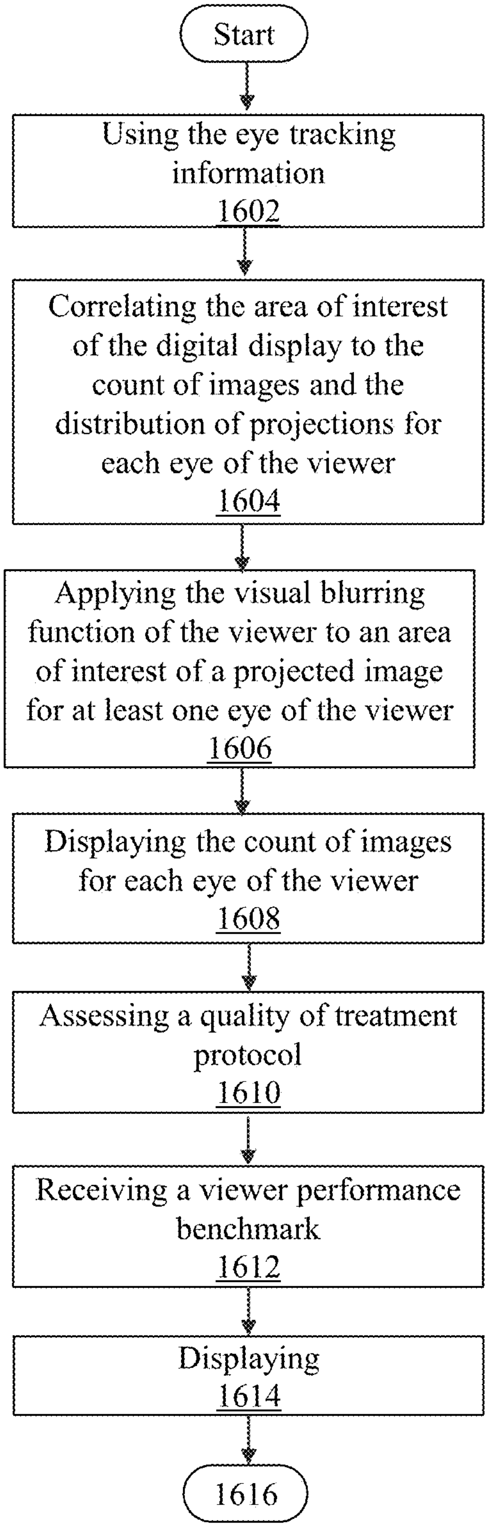
FIG. 16A is a flowchart further illustrating the method for modifying digital media to be displayed on a digital display from FIG. 3, according to some embodiments of the present disclosure.
Figure 16B:
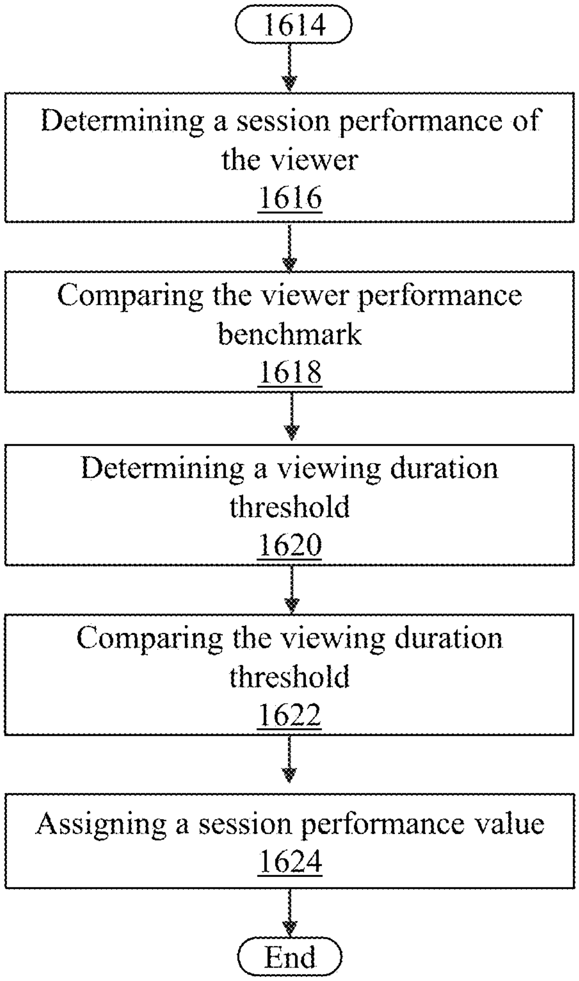
FIG. 16B is a flowchart extending from FIG. 16A and further illustrating the method for modifying digital media to be displayed on a digital display, according to some embodiments of the present disclosure.

In some embodiments, at 1510, the method may include assessing the quality of treatment protocol. In some embodiments, a quality of treatment protocol further comprises, the method may include 1512 to 1518. In some embodiments, receiving a viewer performance benchmark may further comprise a minimum viewing duration threshold. In some embodiments, determining a session performance of the viewer based at least in part on the displayed spatial blurring attribute for the count of images for each eye of the viewer may include steps 1620 to 1624 of FIG. 16. The determining may be based at least in part on the duration. The inferred region of fixation may match the two-dimensional distribution of the projections for each eye of the viewer.

Figure 17A:
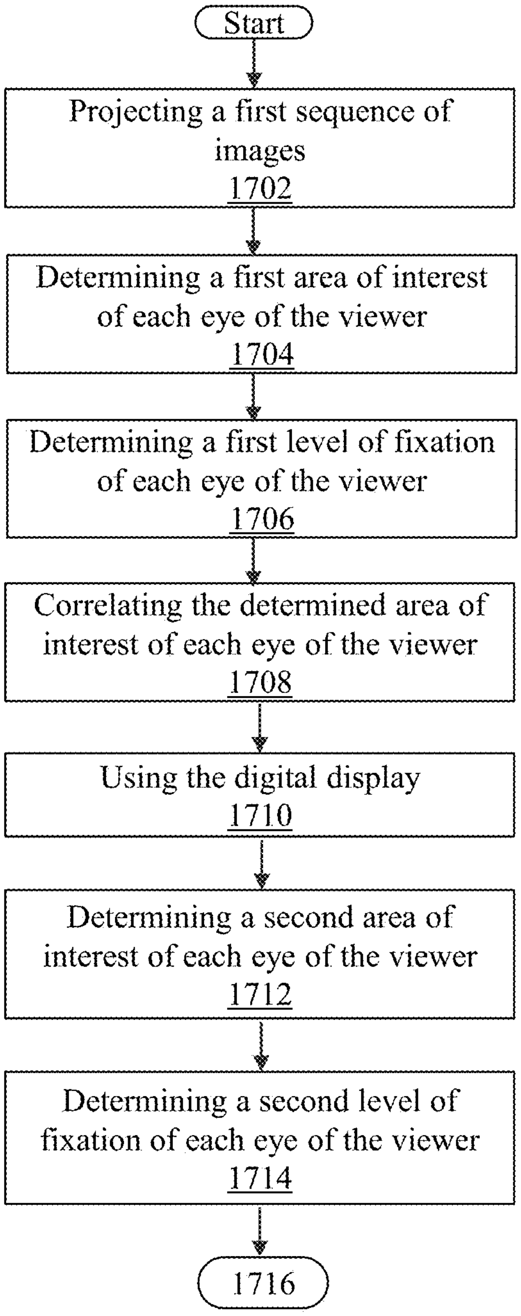
FIG. 17A is a flowchart illustrating a method for assessing a visual acuity of a viewer of a digital display, according to some embodiments of the present disclosure.
Figure 17B:
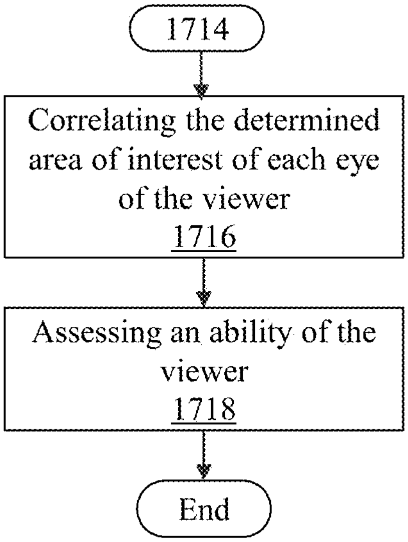
FIG. 17B is a flowchart extending from FIG. 17A and further illustrating the method for assessing a visual acuity of a viewer of a digital display, according to some embodiments of the present disclosure.

FIGS. 17A to 17B are flowcharts that describe a method for assessing a visual acuity of a viewer of a digital display, according to some embodiments of the present disclosure. In some embodiments, at 1702, the method may include projecting a first sequence of images containing at least one object of intertest. At 1704, the method may include determining a first area of interest of each eye of the viewer via a point of regard. At 1706, the method may include determining a first level of fixation of each eye of the viewer. At 1708, the method may include correlating the determined area of interest of each eye of the viewer with the determined fixation of each eye of the viewer.

In some embodiments, at 1710, the method may include using the digital display to project a second sequence of image containing at least one object of intertest in a second location. At 1712, the method may include determining a second area of interest of each eye of the viewer. At 1714, the method may include determining a second level of fixation of each eye of the viewer. At 1716, the method may include correlating the determined area of interest of each eye of the viewer with the determined second area of fixation of each eye of the viewer. At 1718, the method may include assessing an ability of the viewer to follow a movement of the at least one object of interest towards the second location and an ability of the viewer to fixate on the at least one object. The viewer may be a known first distance from the digital display. The viewer may be a known second distance from the digital display.

Figure 18:
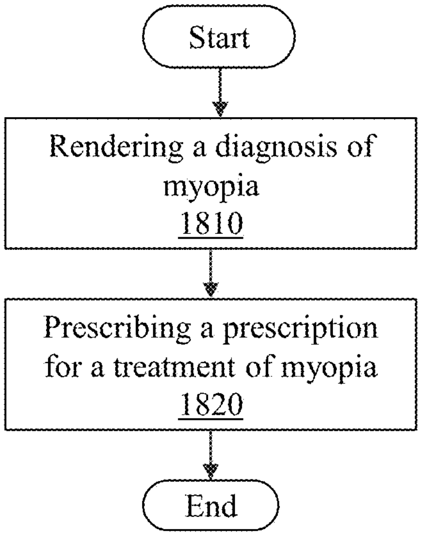
FIG. 18 is a flowchart further illustrating the method for assessing a visual acuity of a viewer of a digital display from FIG. 17A, according to some embodiments of the present disclosure.

FIG. 18 is a flowchart that further describes the method for assessing the visual acuity of a viewer of a digital display from FIG. 17A, according to some embodiments of the present disclosure. In some embodiments, at 1810, the method may include rendering a diagnosis of myopia based at least in part on the assessment of the ability of the viewer to follow a movement of the at least one object of interest towards the second location and an ability of the viewer to fixate on the at least one object. In some embodiments, at 1820, the method may include prescribing a prescription for a treatment of myopia using a digital display. The prescription further comprises, the method may include performing one or more additional steps. A visual blurring function for each of the eyes of the viewer. A myopia treatment protocol.

In some embodiments, the visual blurring function for each of the eyes of the viewer may be associated with the viewer in a digital record, the digital record comprising at least one of, the method may include performing one or more additional steps. A viewer identification, an age-appropriate content for display, an interest appropriate content for digital display, insurance carrier information, a prescribing medical professional, and an access frequency for administering treatment.

Figure 19:
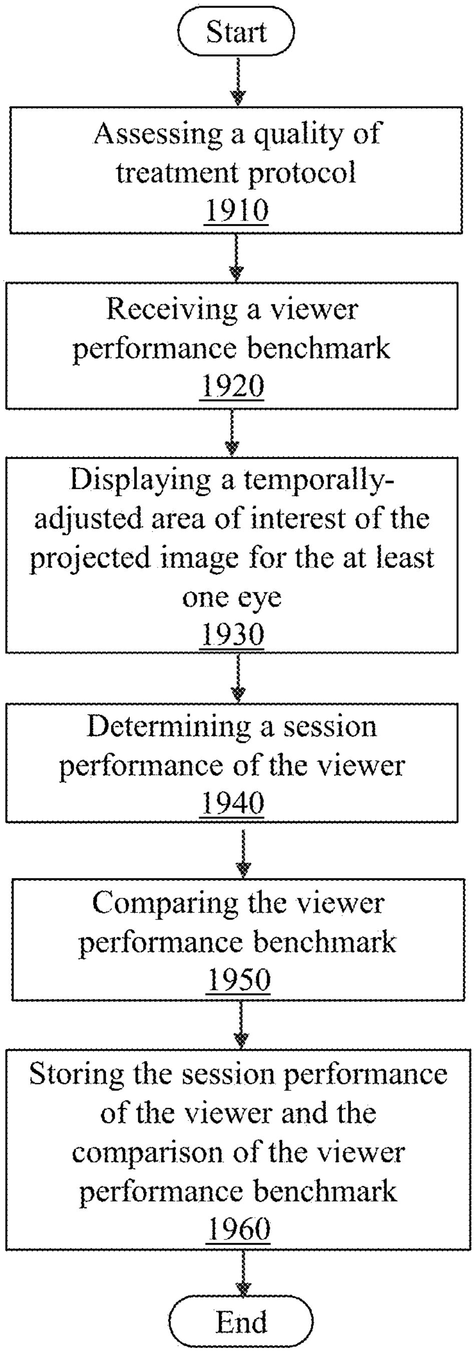
FIG. 19 is a flowchart further illustrating the method for assessing a visual acuity of a viewer of a digital display from FIG. 17A, according to some embodiments of the present disclosure.

FIG. 19 is a flowchart that further describes the method for assessing a visual acuity of a viewer of a digital display from FIG. 17A, according to some embodiments of the present disclosure. In some embodiments, the myopia protocol may further comprise use of prescription eyeglasses, prescription contact lenses, or an orthokeratology in addition to a myopia treatment protocol using a digital display. In some embodiments, at 1910, the method may include assessing the quality of treatment protocol. In some embodiments, a quality of treatment protocol further comprises, the method may include 1920 to 1950. In some embodiments, at 1960, the method may include storing the session performance of the viewer and the comparison of the viewer performance benchmark with the session performance to a digital viewer profile record.

Figure 20A:
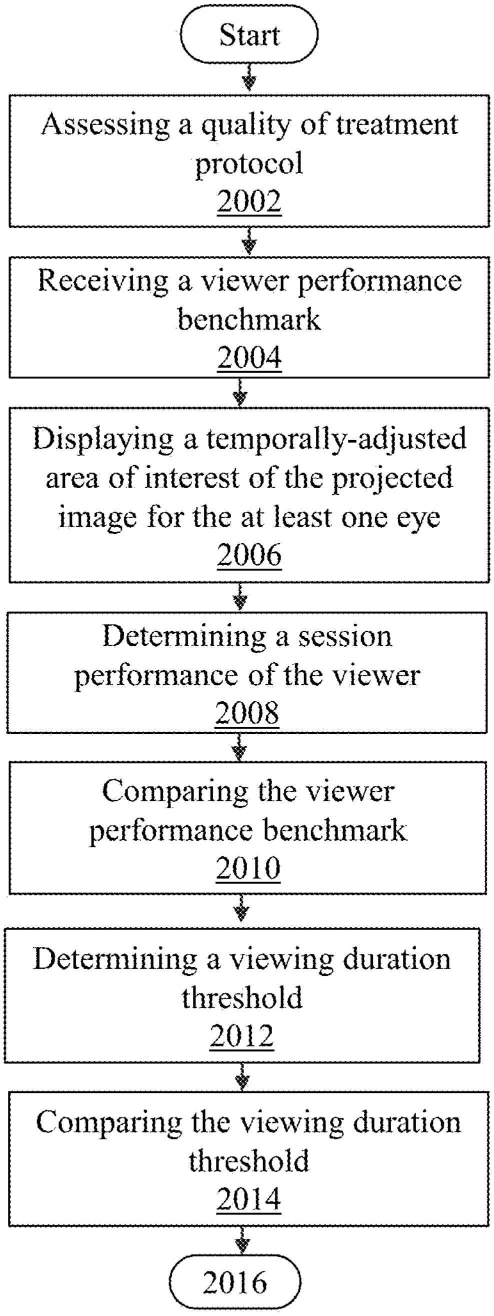
FIG. 20A is a flowchart further illustrating the method for assessing a visual acuity of a viewer of a digital display from FIG. 17A, according to some embodiments of the present disclosure.
Figure 20B:
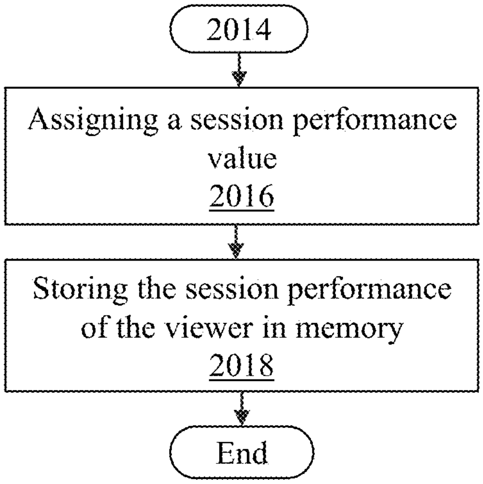
FIG. 20B is a flowchart extending from FIG. 20A and further illustrating the method for assessing a visual acuity of a viewer of a digital display, according to some embodiments of the present disclosure.

FIGS. 20A to 20B are flowcharts that further describe the method for assessing a visual acuity of a viewer of a digital display from FIG. 17A, according to some embodiments of the present disclosure. In some embodiments, the myopia protocol may further comprise use of prescription eyeglasses, prescription contact lenses, or an orthokeratology in addition to a myopia treatment protocol using a digital display. In some embodiments, at 1910, the method may include assessing the quality of treatment protocol. In some embodiments, a quality of treatment protocol further comprises, the method may include 1920 to 1950. Determining whether a viewer viewing a modified digital media is effectively treating a myopia condition may involve several parameters, including but not limited to:

Visual Acuity: Regular measurement of the viewer's visual acuity to help assess whether the myopic condition of the user is progressing or stabilizing. This can be done by displaying eye charts with the viewer positioned at various distances with respect to the digital display.

Change in Prescription: Monitoring changes in the viewer's eyeglass or contact lens prescription over time can provide an indication of how the viewer's myopia is progressing. Changes in prescription may be used to assess aggregated viewer performance data to look for causal effects between the viewer's compliance with the myopia protocol.

Compliance with Treatment: Tracking how regularly the viewer uses the modified digital media as prescribed and for the appropriate duration can be a strong indicator of the effectiveness of the treatment.

Digital Interaction Data: Information such as gaze direction, fixation region, and duration can provide insights into whether the viewer is interacting with the digital media in the intended manner.

Performance during Visual Tasks: Regular observation and testing of the viewer's ability to perform certain visual tasks, both close-up and at a distance, can also be indicative of the treatment's effectiveness.

Subjective Feedback: The viewer's own feedback about their vision and comfort while viewing the digital media can also be valuable. Such feedback may be periodically solicited before, during, or after the administration of the myopia protocol.

In some embodiments, at 2012, the method may include determining a viewing duration threshold. At 2014, the method may include comparing the viewing duration threshold with the viewer performance benchmark. At 2016, the method may include assigning a session performance value based on the comparison. At 2018, the method may include storing the session performance of the viewer in memory. The determining may be based at least in part on the duration. The inferred region of fixation may match the two-dimensional distribution of the projections for each eye of the viewer.

Figure 21:
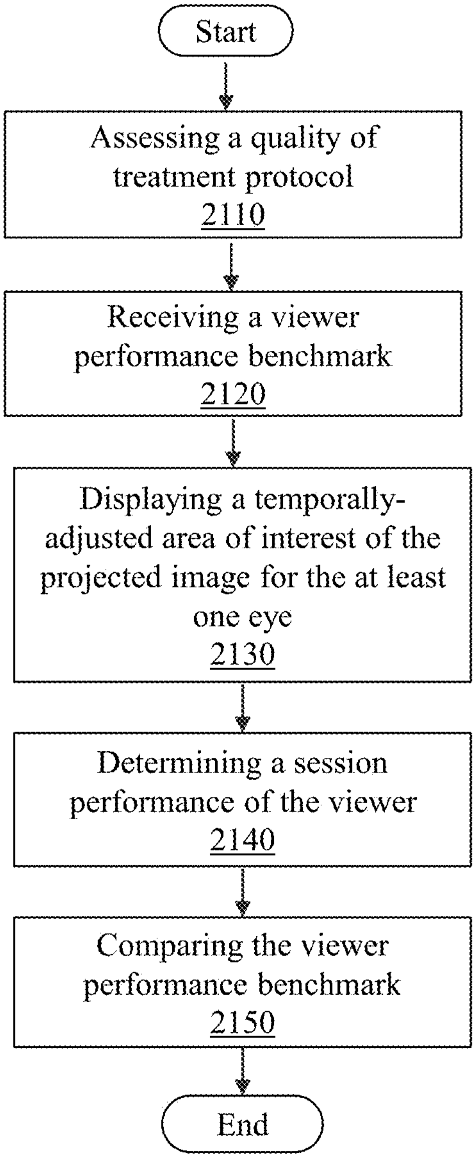
FIG. 21 is a flowchart further illustrating the method for assessing a visual acuity of a viewer of a digital display from FIG. 17A, according to some embodiments of the present disclosure.

FIG. 21 is a flowchart that further describes the method for assessing a visual acuity of a viewer of a digital display from FIG. 17A, according to some embodiments of the present disclosure. In some embodiments, the myopia protocol may further comprise use of prescription eyeglasses, prescription contact lenses, or an orthokeratology in addition to a myopia treatment protocol using a digital display. In some embodiments, at 1910, the method may include assessing a quality of treatment protocol. In some embodiments, a quality of treatment protocol further comprises, the method may include 1920 to 1950. In some embodiments, receiving a viewer performance benchmark may further comprise a viewer performance of the viewer at a first distance and at least one second distance.

Figure 22A:
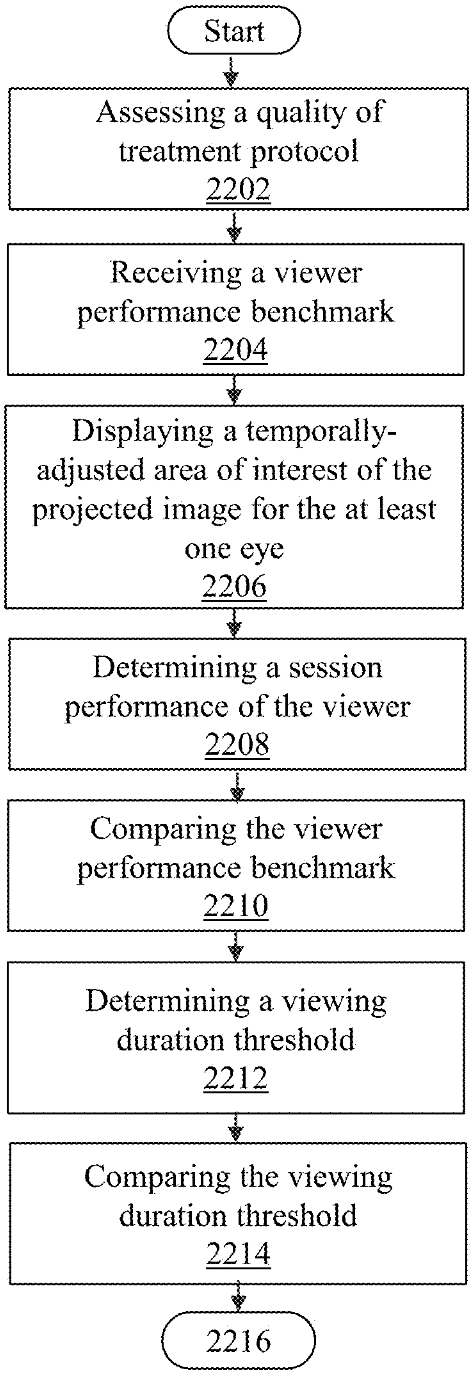
FIG. 22A is a flowchart further illustrating the method for assessing a visual acuity of a viewer of a digital display from FIG. 17A, according to some embodiments of the present disclosure.
Figure 22B:
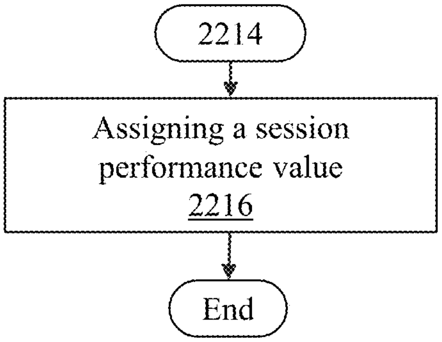
FIG. 22B is a flowchart extending from FIG. 22A and further illustrating the method for assessing a visual acuity of a viewer of a digital display, according to some embodiments of the present disclosure.

FIG. 22A and FIG. 22B are flowcharts that further describe the method for assessing a visual acuity of a viewer of a digital display from FIG. 17A, according to some embodiments of the present disclosure. In some embodiments, the myopia protocol may further comprise use of prescription eyeglasses, prescription contact lenses, or an orthokeratology in addition to a myopia treatment protocol using a digital display. In some embodiments, at 1910, the method may include assessing a quality of treatment protocol. In some embodiments, a quality of treatment protocol further comprises, the method may include 1920 to 1950.

In some embodiments, receiving a viewer performance benchmark may further comprise a minimum viewing duration threshold. In some embodiments, determining a session performance of the viewer based at least in part on the displayed spatial blurring attribute for the count of images for each eye of the viewer further comprises, the method may include 2212 to 2216. The determining may be based at least in part on the duration. The inferred region of fixation may match the two-dimensional distribution of the projections for each eye of the viewer.

Figure 23:
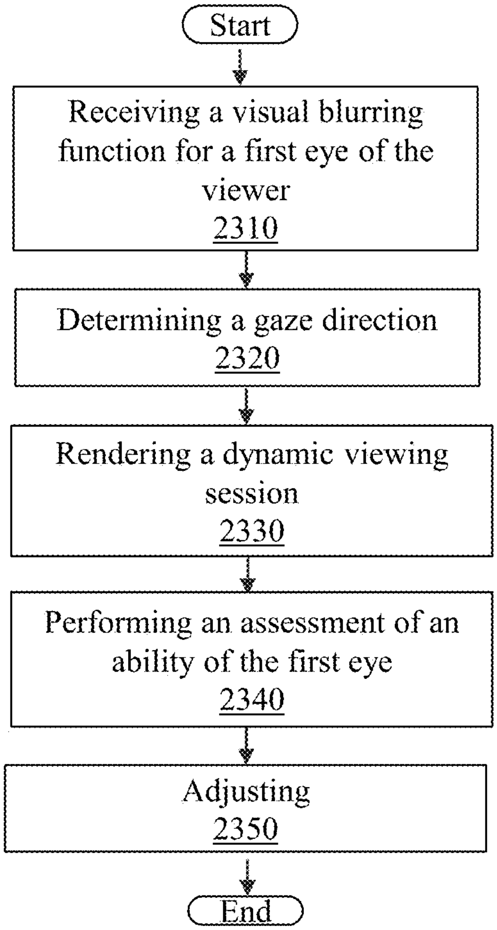
FIG. 23 is a flowchart illustrating a method for treating myopia, according to some embodiments of the present disclosure.

FIG. 23 is a flowchart that describes a method for treating myopia, according to some embodiments of the present disclosure. In some embodiments, at 2310, the method may include receiving a visual blurring function for a first eye of the viewer. At 2320, the method may include determining a gaze direction, a distance between the viewer and the digital display, and the point of regard of the first eye of the viewer with regard to the digital display. At 2330, the method may include rendering a dynamic viewing session containing at least one area of interest.

In some embodiments, at 2340, the method may include performing an assessment of an ability of the first eye to follow a movement of the at least one area of interest and an ability of the first eye of the viewer to fixate on the at least one object. At 2350, the method may include adjusting spatially and temporally the at least one area of interest in the rendered dynamic viewing session based at least in part on the assessment. The dynamic viewing session may comprise a plurality of images for display by the digital display for the first eye, the rendering based at least in part on the visual blurring function for the first eye, the determined gaze direction, the distance between the viewer and the digital display, and the point of regard of the first eye of the viewer, and the at least one area of interest.

Figure 24A:
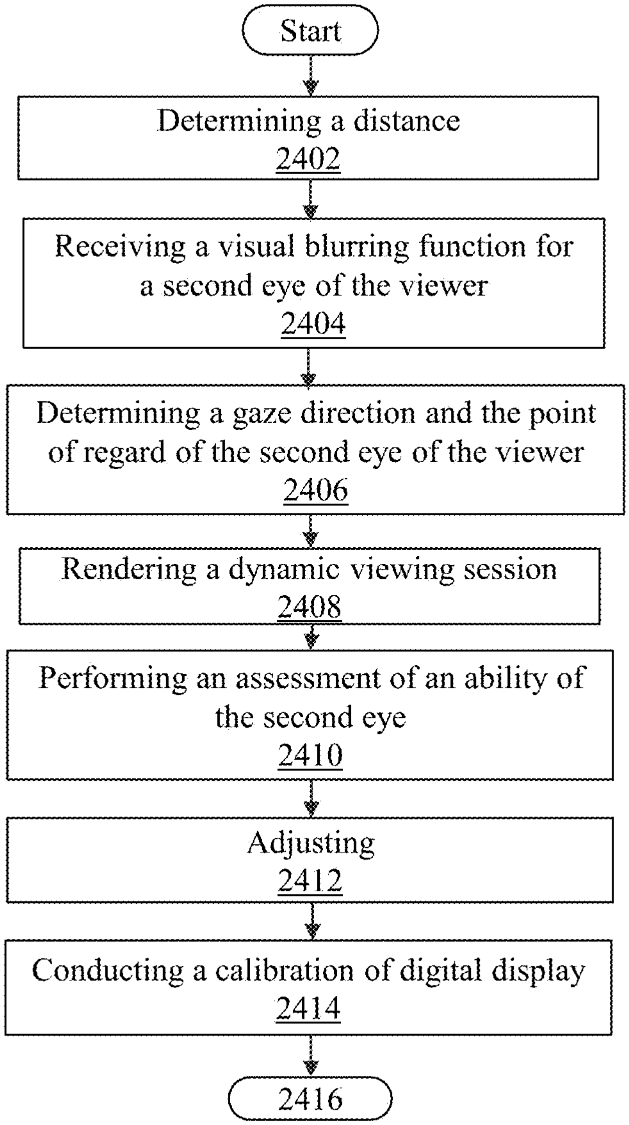
FIG. 24A is a flowchart further illustrating the method for treating myopia from FIG. 23, according to some embodiments of the present disclosure.
Figure 24B:
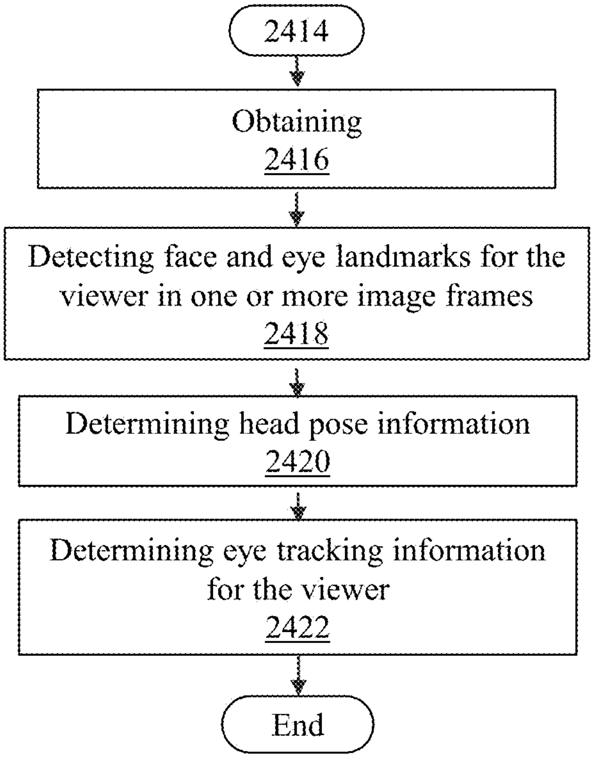
FIG. 24B is a flowchart extending from FIG. 24A and further illustrating the method for treating myopia, according to some embodiments of the present disclosure.

FIG. 24A to 24B are flowcharts that further describe the method for treating myopia from FIG. 23, according to some embodiments of the present disclosure. In some embodiments, at 2402, the method may include determining a distance between the viewer and the digital display. At 2404, the method may include receiving a visual blurring function for a second eye of the viewer. At 2406, the method may include determining a gaze direction and the point of regard of the second eye of the viewer with regard to the digital display. At 2408, the method may include rendering a dynamic viewing session containing at least one area of interest.

In some embodiments, at 2410, the method may include performing an assessment of an ability of the second eye to follow a movement of the at least one area of interest and an ability of the second eye of the viewer to fixate on the at least one area of interest at the distance. At 2412, the method may include adjusting spatially and temporally at least one area of interest in the rendered dynamic viewing session based at least in part on the assessment. The dynamic viewing session may comprise a plurality of images for display by the digital display for the second eye, the rendering based at least in part on the visual blurring function for the second eye, the determined gaze direction, and the point of regard of the second eye of the viewer, the distance between the viewer and the digital display, and the at least one area of interest.

In some embodiments, the method. At 2414, the method may include conducting a calibration of digital display. In some embodiments, conducting a calibration of digital display may include 2416 to 2422. Data collected may include a point of regard (PoR) of each eye of the viewer, an eye state of each eye of the viewer, a gaze direction of each eye of the viewer, an eye landmark illumination information for each eye of the viewer, and a position of each eye of the viewer relative to the digital display.

Figure 25:
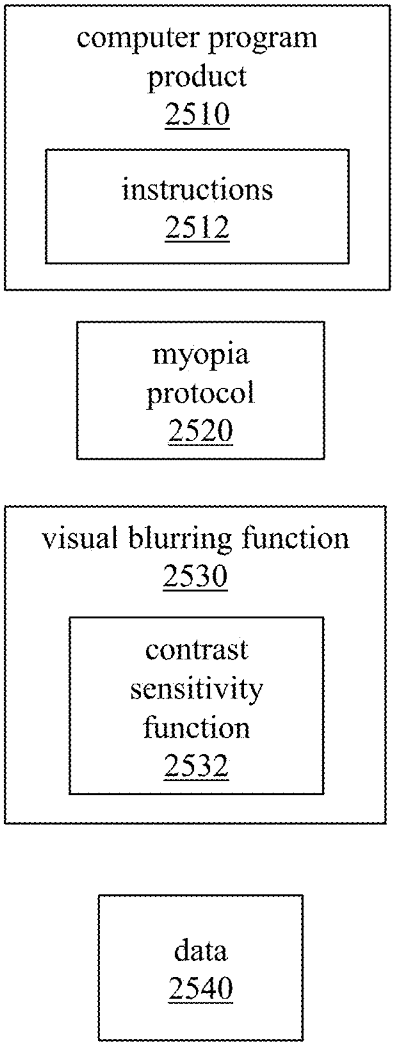
FIG. 25 is a block diagram further illustrating the computer program product from FIG. 3, according to some embodiments of the present disclosure.

FIG. 25 is a block diagram that further describes the computer program product 310 from FIG. 3, according to some embodiments of the present disclosure. In some embodiments, testing a visual acuity of the viewer to the applied area of interest. In some embodiments, the visual blurring function 2530 may include a contrast sensitivity function 2532 (CSF) indicative of a visual acuity field of the viewer. In some embodiments, the computer program product may include a contrast sensitivity function (CSF) indicative of a visual acuity of the viewer. In some embodiments, the computer program product may include instructions 2512 for testing a visual acuity of the viewer to the applied area of interest. In some embodiments, the visual blurring function 2530 may include a contrast sensitivity function 2532 (CSF) indicative of a visual acuity field of the viewer. In some embodiments, a contrast sensitivity function (CSF) is indicative of the visual acuity of the viewer. In some embodiments, the instructions 2512 may include a mathematical function a treatment function for each eye of the viewer; a two-dimensional boundary of a Point of Regard for each eye of the viewer; a distance between at least one eye of the viewer and the two-dimensional boundary of the area of focus for at least one eye of the viewer; and at least one projection.

In some embodiments, rendering a first two-dimensional treatment area in a two-dimensional boundary of a Point of Regard for each eye of the viewer based at least in part on the mathematical function at time $t_0$ and a distance between the viewer and the digital display. Displaying the rendering of the first two-dimensional treatment area in the two-dimensional boundary of a Point of Regard for each eye of the viewer. Determining a visual acuity field for each eye of the viewer in response to the displayed rendering of the first treatment area for each eye of the viewer at time $t_0$ and the distance between the viewer and the digital display.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having ordinary skill in the art will recognize that the state of the art has progressed to the point where there is little distinction left between hardware, software, and/or firmware implementations of aspects of systems; the use of hardware, software, and/or firmware is generally a design choice representing cost vs. efficiency tradeoffs (but not always, in that in certain contexts the choice between hardware and software can become significant). Those having ordinary skill in the art will appreciate that there are various vehicles by which processes and/or systems and/or other technologies described herein can be affected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be affected, none of which is inherently superior to the other in that any vehicle to be utilized is a choice dependent upon the context in which the vehicle will be deployed and the specific concerns (e.g., speed, flexibility, or predictability) of the implementer, any of which may vary.

In some implementations described herein, logic and similar implementations may include software or other control structures suitable to operation. Electronic circuitry, for example, may manifest one or more paths of electrical current constructed and arranged to implement various logic functions as described herein. In some implementations, one or more medias are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively, or additionally, in some variants, an implementation may include special-purpose hardware, software, firmware components, and/or general-purpose components executing or otherwise controlling special-purpose components. Specifications or other implementations may be transmitted by one or more instances of tangible or transitory transmission media as described herein, optionally by packet transmission or otherwise by passing through distributed media at various times.

Alternatively, or additionally, implementations may include executing a special-purpose instruction sequence or otherwise operating circuitry for enabling, triggering, coordinating, requesting, or otherwise causing one or more occurrences of any functional operations described above. In some variants, operational or other logical descriptions herein may be expressed directly as source code and compiled or otherwise expressed as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar modes of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those having ordinary skill in the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a USB drive, a solid state memory device, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read-only, etc.)), and/or electrical circuitry forming a communications device (e.g., a modem, communications switch, optical-electrical equipment, etc.). Those having ordinary skill in the art will recognize that the subject matter described herein may be implemented in an analog or digital fashion or some combination thereof.

Those skilled in the art will recognize that at least a portion of the devices and/or processes described herein can be integrated into a data processing system. Those having ordinary skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

In certain cases, use of a system or method as disclosed and claimed herein may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory.

Further, implementation of at least part of a system for performing a method in one territory does not preclude use of the system in another territory.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

One skilled in the art will recognize that the herein described components (e.g., operations), devices, objects, and the discussion accompanying them are used as examples for the sake of conceptual clarity and that various configuration modifications are contemplated. Consequently, as used herein, the specific examples set forth and the accompanying discussion are intended to be representative of their more general classes. In general, use of any specific example is intended to be representative of its class, and the non-inclusion of specific components (e.g., operations), devices, and objects should not be taken to be limiting.

With respect to the use of substantially any plural and/or singular terms herein, those having ordinary skill in the art can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are presented merely as examples, and that in fact many other architectures may be implemented which achieve the same functionality. In a conceptual sense, any arrangement of components to achieve the same functionality is effectively "associated" such that the desired functionality is achieved. Therefore, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of "operably couplable" include but are not limited to physically mateable or physically interacting components, wirelessly interactable components, wirelessly interacting components, logically interacting components, or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components, inactive-state components, or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such a recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having ordinary skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having ordinary skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented as sequences of operations, it should be understood that the various operations may be performed in other orders than those which are illustrated or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting.

What is claimed is:

1. A digital display system for treating myopia, the system comprising:

a. at least one forward looking camera;

b. a digital display;

c. at least one graphical processing unit (GPU) to render digital content to the display;

d. at least one central processing unit (CPU) wherein the central processing unit contains instructions that when executed cause the system to carry out the following steps:

receiving digital media; receiving face image data, receiving eye landmark image data for a viewer within a field of view of at least one camera in proximity to a viewer, and receiving a distance between the digital display and a viewer;

determining a cone of vision, wherein a gaze direction, the cone of vision, and the distance between the digital display and the viewer is used to infer a region of fixation;

receiving a visual blurring function for each eye of the viewer;

determining a count of images and an area of interest within the boundaries of a frame of each image, the area of interest based at least in part on eye tracking information; and applying a spatial blurring attribute for the count of images for each eye of the viewer based at least in part on the received visual blurring function of the viewer, the determined area of interest, and the myopia protocol.

2. The system of claim 1, wherein the myopia protocol is at least one of a myopia diagnosis protocol, a myopia treatment protocol, and a quality of treatment protocol.

3. The system of claim 2, wherein the myopia diagnosis protocol is based at least in part on a visual acuity test, a refraction test, a retinoscopy, an autorefractor, and a dilated eye exam.

4. The system of claim 2, wherein the myopia treatment protocol further comprises use of prescription eyeglasses, prescription contact lenses, and an orthokeratology.

5. The system of claim 4, wherein the myopia treatment protocol further comprises use of prescription eyeglasses, prescription contact lenses, and an orthokeratology outside of a viewing session in which the modified digital media is displayed on the digital display.

6. The system of claim 2, wherein the quality of treatment protocol further comprises:

a. receiving a viewer performance benchmark;

b. displaying the spatial blurring attribute for the count of images for each eye of the viewer based at least in part on the received visual blurring function of the viewer and the myopia protocol;

c. determining a session performance of the viewer based at least in part on the displayed spatial blurring attribute for the count of images for each eye of the viewer; and d. comparing the viewer performance benchmark with the session performance.

7. The system of claim 6, further comprises:

e. determining a viewing duration threshold, wherein the determining is based at least in part on the duration in which the inferred region of fixation matches the two-dimensional distribution of the projections for each eye of the viewer;

f. comparing the viewing duration threshold with the viewer performance benchmark;

g. assigning a session performance value based on the comparison; and h. storing the session performance of the viewer in memory.

8. The system of claim 6, wherein receiving a viewer performance benchmark further comprises a minimum viewing duration threshold.

9. The system of claim 8, wherein determining a session performance of the viewer based at least in part on the displayed spatial blurring attribute for the count of images for each eye of the viewer further comprises:

i. determining a viewing duration threshold, wherein the determining is based at least in part on the duration in which the inferred region of fixation matches the two-dimensional distribution of the projections for each eye of the viewer;

j. comparing the viewing duration threshold with the minimum viewing duration threshold; and k. assigning a session performance value based on the comparison.

10. The system of claim 2, wherein the quality of treatment protocol further comprises associating at least one parameter of the quality of treatment protocol with a viewer profile.

11. The system of claim 10, wherein the at least one parameter of the quality of treatment protocol further comprises:

l. a current visual acuity measurement;

m. an indication of a progression status of a myopia condition;

n. an eye health examination;

o. a compliance parameter;

p. a myopia treatment prescription; and q. a session performance value.

12. The system of claim 1, wherein receiving digital media further comprises:

r. opening a media viewing application;

s. receiving user credentials associated with a viewer profile; and t. loading the digital media in the media viewing application.

13. The system of claim 12, wherein a media viewing application is a myopia treatment application.

14. The system of claim 1, wherein receiving digital media further comprises receiving at a processor digital media from at least one of a streaming service, a dedicated media device, a video gaming console, an online gaming service, a social media site, and a live streaming service.

15. The system of claim 1, wherein the digital media is at least one of a podcast, a social media post, a live streaming event, a video game, a webpage, an e-book, a video call, augmented reality information, and a virtual reality environment.

16. The system of claim 1, wherein the digital media is at least one of a still image, a video, a movie, a television program, a social media content, and specialized content for the treatment of myopia.

17. The system of claim 1, wherein receiving digital media further comprises receiving the digital media at least one of the CPU and GPU via one or more of a wireless streaming service, a connected media player, a network attached storage (NAS) device, and a gaming system.

18. The system of claim 1, wherein receiving a visual blurring function of the viewer further comprises:

receiving a contrast sensitivity function (CSF) indicative of a visual acuity field of the viewer.

19. The system of claim 18, wherein a contrast sensitivity function (CSF) indicative of a visual acuity of the viewer further comprises:

data indicative of a performance of a contrast function sensitivity performance.

20. The system of claim 18, wherein a contrast sensitivity function (CSF) indicative of a visual acuity of the viewer further comprises:

a mathematical function for a Visual Blurring Function (VBF) as a function of time, wherein the mathematical function further comprises at least one variable for each of:

i. a treatment function for each eye of the viewer;

ii. a two-dimensional boundary of a Point of Regard for each eye of the viewer;

iii. a distance between at least one eye of the viewer and the two-dimensional boundary of the area of focus for at least one eye of the viewer; and iv. at least one projection.

21. The system of claim 20, further comprises:

a) rendering a first two-dimensional treatment area for each eye of the viewer based at least in part on the mathematical function at time $t_0$;

b) displaying the rendering of the first two-dimensional treatment area for each eye of the viewer; and c) determining a visual acuity field for each eye of the viewer in response to the displayed rendering of the first treatment area for each eye of the viewer at time $t_0$.

22. The system of claim 21, further comprising:

a) comparing the visual acuity performance for each eye of the viewer at time $t_0$ with a historical visual acuity performance for each eye of the viewer; and b) updating the visual blurring function for at least one eye of the viewer if the comparison indicates a change in the visual acuity performance for the at least one eye.

23. The system of claim 22, wherein the updating the visual blurring function for at least one eye of the viewer if the comparison indicates a change in the visual acuity performance for the at least one eye, the change in visual acuity further comprises at least one of an indication of an improvement in visual acuity and a deterioration in visual acuity.

24. The system of claim 18, wherein a contrast sensitivity function (CSF) indicative of a visual acuity of the viewer further comprises:

data indicative of a performance of a spatial frequency sensitivity performance.

25. The system of claim 18, wherein a contrast sensitivity function (CSF) indicative of a visual acuity of the viewer further comprises:

a function indicative of a visual acuity performance of the user at a distance from the digital display and its minimal Spatial Frequency Threshold for a trackable object on the digital display.

26. The system of claim 18, wherein receiving a visual blurring function of the viewer further comprises:

receiving viewer digital identification data indicative of the viewer;

transmitting a request for a visual acuity profile of the viewer;

receiving the visual acuity profile wherein the visual acuity profile includes at least the visual blurring function of the viewer and a myopia treatment protocol.

27. The system of claim 18, wherein receiving the visual acuity profile further comprises a myopia assessment for each eye of the viewer.

28. The system of claim 1, wherein receiving a visual blurring function of the viewer further comprises:

receiving a contrast sensitivity function (CSF), wherein the contrast sensitivity function (CSF) further comprises at least one instruction for applying the spatial blurring attribute based at least in part on the received visual blurring function of the viewer and the myopia protocol.

29. The system of claim 28, wherein applying a spatial blurring attribute for the count of images for each eye of the viewer based at least in part on the received visual blurring function of the viewer and the myopia protocol further comprises at least one instruction for determining the spatial blurring attribute for the count of images for each eye of the viewer based at least in part on one or more visual acuity fields of the viewer, the one or more visual acuity field, wherein the visual acuity field further comprises at least one of:

a foveal visual acuity field;

a parafoveal visual acuity field; and a peripheral visual acuity field.

30. The system of claim 1, further comprising:

displaying the count of images for each eye of the viewer based on the received visual blurring function of the viewer.

31. The system of claim 30, wherein displaying the count of images for each eye of the viewer based on the received visual blurring function of the viewer further comprises:

dynamically altering the spatial blurring attribute for the count of images for each eye of the viewer as a function of time.

32. The system of claim 31, wherein dynamically altering the spatial blurring attribute for the count of images for each eye of the viewer as a function of time further comprises:

altering the dimensions of the area of the spatial blurring attribute within the foveal visual acuity field of an eye of the viewer as a function of time.

33. The system of claim 32, wherein altering the dimensions of the area of the spatial blurring attribute to maintain a cognitive load further comprises:

inferring the cognitive load from the eye tracking information.

34. The system of claim 31, wherein dynamically altering the spatial blurring attribute for the count of images for each eye of the viewer as a function of time further comprises:

altering the dimensions of the area of the spatial blurring attribute within the foveal visual acuity field of an eye of the viewer as a sinusoidal function of time.

35. The system of claim 31, wherein dynamically altering the spatial blurring attribute for the count of images for each eye of the viewer as a function of time further comprises:

altering the dimensions of the area of the spatial blurring attribute within the foveal visual acuity field of an eye of the viewer, wherein altering the dimensions of the area of the spatial blurring attribute to maintain a cognitive load.

36. The system of claim 1, wherein applying a spatial blurring attribute for the count of images for each eye of the viewer based at least in part on the received visual blurring function of the viewer and the myopia protocol further comprises:

determining the count of images based at least in part on one or more of a refresh rate of the digital display, a defined segment of video, a sampling rate of at least one camera of the digital display, and the visual blurring function for each eye of the viewer.

37. The system of claim 1, wherein applying a spatial blurring attribute for the count of images for each eye of the viewer based at least in part on the received visual blurring function of the viewer and the myopia protocol further comprises:

using the eye tracking information to determine an area of interest of the digital display;

correlating the area of interest of the digital display to the count of images for each eye of the viewer;

applying the visual blurring function of the viewer to an area of interest of a projected image for at least one eye of the viewer.

38. The system of claim 37, wherein applying the visual blurring function of the viewer to an area of interest of a projected image for the at least one eye of the viewer further comprises: spatially-adjusting the area of interest of the projected image for the at least one eye based at least in part on the myopia treatment protocol.

39. The system of claim 1, further comprising:

using the eye tracking information to determine an area of interest via the point-of-regard of the digital display;

correlating the area of interest of the digital display to the count of images and the distribution of projections for each eye of the viewer;

applying the visual blurring function of the viewer to an area of interest of a projected image for at least one eye of the viewer;

spatially-adjusting the area of interest of the projected image for the at least one eye; and displaying the count of images for each eye of the viewer based on the received visual blurring function of the viewer.

40. The system of claim 39, wherein spatially-adjusting the area of interest of the projected image for the at least one eye further comprises:

a) temporally-adjusting the application of the visual blurring function of the viewer to the area of interest of the projected image for at least one eye of the viewer; and b) monitoring the accumulated period in which the visual blurring function of the viewer is applied to the area of interest of the projected image for at least one eye of the viewer.

41. The system of claim 1, further comprising:

using the eye tracking information to determine an area of interest via the point-of-regard of the digital display;

correlating the area of interest of the digital display to the count of images and the distribution of projections for each eye of the viewer;

applying the visual blurring function of the viewer to an area of interest of a projected image for at least one eye of the viewer;

temporally-adjusting the area of interest of the projected image for the at least one eye; and displaying the count of images for each eye of the viewer based on the received visual blurring function of the viewer.

42. The system of claim 41, further comprising monitoring the accumulated period in which the visual blurring function of the viewer is applied to the area of interest of the projected image for at least one eye of the viewer.

43. The system of claim 41, further comprising assessing a quality of treatment protocol.

44. The system of claim 43, wherein a quality of treatment protocol further comprises:

a) receiving a viewer performance benchmark;

b) displaying temporally-adjusting the area of interest of the projected image for the at least one eye based at least in part on the received visual blurring function of the viewer and the myopia protocol;

c) determining a session performance of the viewer based at least in part on the displayed spatial blurring attribute for the count of images for each eye of the viewer; and d) comparing the viewer performance benchmark with the session performance.

45. The system of claim 44, further comprises:

a) determining a viewing duration threshold, wherein the determining is based at least in part on the duration in which the inferred region of fixation matches the two-dimensional distribution of the projections for each eye of the viewer;

b) comparing the viewing duration threshold with the viewer performance benchmark;

c) assigning a session performance value based on the comparison; and d) storing the session performance of the viewer in memory.

46. The system of claim 44, wherein receiving a viewer performance benchmark further comprises a minimum viewing duration threshold.

47. The system of claim 46, wherein determining a session performance of the viewer based at least in part on the displayed spatial blurring attribute for the count of images for each eye of the viewer further comprises:

a) determining a viewing duration threshold, wherein the determining is based at least in part on the duration in which the inferred region of fixation matches the two-dimensional distribution of the projections for each eye of the viewer;

b) comparing the viewing duration threshold with the minimum viewing duration threshold; and c) assigning a session performance value based on the comparison.

* * * * *